US006656465B2

(12) United States Patent
Clary et al.

(10) Patent No.: US 6,656,465 B2
(45) Date of Patent: Dec. 2, 2003

(54) ANTIBODIES THAT MIMIC ACTIONS OF NEUROTROPHINS

(76) Inventors: Douglas O. Clary, San Francisco, CA (US); Gisela Weskamp, New York, NY (US); Leeann R. Austin, San Francisco, CA (US); Louis F. Reichardt, San Francisco, CA (US)

( * ) Notice: Subject to any disclaimer, the term of this patent is extended or adjusted under 35 U.S.C. 154(b) by 147 days.

(21) Appl. No.: 09/770,949

(22) Filed: Jan. 26, 2001

(65) Prior Publication Data

US 2002/0054874 A1 May 9, 2002

Related U.S. Application Data

(63) Continuation of application No. 09/033,313, filed on Mar. 2, 1998, now abandoned, which is a continuation of application No. 08/466,839, filed on Jun. 6, 1995, now abandoned, which is a continuation of application No. 08/162,597, filed on Dec. 3, 1993, now Pat. No. 5,753,225.

(51) Int. Cl.[7] ....................... A61K 39/395; C07K 16/00

(52) U.S. Cl. ................................ 424/130.1; 424/138.1; 424/141.1; 424/143.1; 424/156.1; 530/387.1; 530/388.1; 530/388.22

(58) Field of Search ........................... 424/130.1, 138.1, 424/141.1, 143.1, 156.1; 530/387.1, 388.1, 388.22

(56) References Cited

U.S. PATENT DOCUMENTS

| | | | |
|---|---|---|---|
| 5,231,001 | A | 7/1993 | Kaplan et al. |
| 5,753,225 | A | 5/1998 | Clary et al. |
| 5,877,305 | A | 3/1999 | Huston et al. |

FOREIGN PATENT DOCUMENTS

| | | | |
|---|---|---|---|
| EP | 0471205 | A1 | 2/1992 |
| EP | 92/16559 | A1 | 10/1992 |
| WO | WO 92/18149 | A1 | 10/1992 |

OTHER PUBLICATIONS

Alberts, et al. "Molecular Biology of the Cell" *Garland Publishing Inc. (N.Y)* (1989), pp. 333–334.

Barde, Y.A., "Tropic Factors and Neuronal Survival" *Neuron.* (1989) vol. 2, pp. 1525–1534.

Barker, et al. "The Nerve Growth Factor Receptor: A Multicomponent System that Mediates the Actions of the Neurotrophin Family of Proteins" *Molecular and Cellular Biochemistry* (1992) vol. 110, p. 1–15.

Bolhuis, et al. "Functional Expression of a Single Chain FV/γ Receptor with Renal Cell Carcinoma Specificity in Activated Human PBL" *Third Meeting of the European Working Group of Human Gene Transfer and Therapy, Barcelona, Spain* (Nov. 17–20, 1995) *Gene Therapy 2* (*Suppl. 1*):S21 ISSN: 0969–7128.

Bolhuis, et al. "ScFv/gamma Antibody Receptors on Human Cytotoxic T Lymphocytes (CTL) Bind Antigen, Transduce Activation Signals and Respond to Co–regulatory Signals" *Joint Meeting of the American Academy of Allergy, Asthma and Immunology, the American Association of Immunologists and the Clinical Immunology Society San Francisco, California, USA* (Feb. 21–26, 1997) *J. Allergy Clin Immunol 99* (1,Pt2):S116, 1997 ISSN: 0091–6749.

Casten, et al. "Anti–immunoglobulin Augments the B–Cell Antigen–presentation Function Independently of Internalization of Receptor–Antigen Complex" *Proc. Natl. Acad. Sci. USA* (Sep. 1985) vol. 82, pp. 5890–5894.

Collazo, et al. "Cellular Targets and Trophic Functions of Neurotrophin–3 in the Developing Rat Hippocampus" *Neuron* (Oct. 1992) vol. 9, pp. 643–656.

Cordon–Cardo, et al. "The trk Tyrosine Protein Kinase Mediates the Mitogenic Properties of Nerve Growth Factor and Neurotrophin–3" *Cell* (1991) vol. 66, pp. 173–183.

Drebin, et al. "Down–Modulation of an Oncogene Protein Product and Reversion of the Transformed Phenotype by Monoclonal Antibodies" *Cell* (Jul. 1985) vol. 41, pp. 695–706.

Eager, K. "Molecular Characterization of Human trk Proto–oncogene product Monoclonal Antibodies" *Onc.* (May 1991) vol. 6(5), pp. 819–824.

Eide, et al. "Neurotrophins and Their Receptors–Current Concepts and Implications for Neurologic Disease" *Exp. Neurol.* (1993) vol. 121, pp. 200–214.

Fan, et al. "Regulation of Epidermal Growth Factor Receptor in NIH3T3/HER14 Cells by Antireceptor Monoclonal Antibodies" *J. of Biological Chemistry* (Oct. 1993) vol. 268 (28), pp. 21073–21079.

Fraser, et al. "TCP–11, the Product of a Mouse t–complex Gene, Plays a Role in Stimulation of Capacitation and Inhibition of the Spontaneous Acrosome Reaction" *Molocular Reproduction and Development* (1997), vol. 48, pp. 375–382.

Greene, et al. "Establishment of a Noradrenergic Clonal Line of Rat Adrenal Pheochromocytoma Cells Which Respond to Nerve Growth Factor" *Proc. Natl. Acad. Sci. USA* (1976) vol. 73, pp. 2424–2428.

Goroff, et al. "Participation of IgGFe Receptor (FeγR) in in vivo B–cell Activation by a Monovalent Anti–IgD Antibody (Ab) Fragment" *Fed Proc* (1987) vol. 46(4), pp. 1204.

Hanks, et al. "The Protein Kinase Family: Conserved Features and Deduced Phylogeny of the Catalytic Domains" *Science* (1988) vol. 241, pp. 42–52.

Holzer, et al. "A Fusion Protein of IL–8 and a Fab Antibody Fragment Binds to IL–8 Receptors and Induces Neutrophil Activation" *Cytokine* (Mar. 1996) vol. 8(3), pp. 214–221.

(List continued on next page.)

*Primary Examiner*—Gary Kunz
*Assistant Examiner*—Stephen Gucker

(57) ABSTRACT

The use and production of immunoglobulins which activate trk receptors and imitate effects of neurotrophins are provided. Immunoglobulins which block trk receptor activation and methods of use are also provided.

6 Claims, 4 Drawing Sheets

OTHER PUBLICATIONS

Holtzman, et al. "p140$^{trk}$ mRNA Marks NGF–Responsive Forebrain Neurons: Evidence that trk Gene Expression is Induced by NGF" *Neuron* (1992) vol. 9, pp. 465–478.

Hosang, et al. "Molecular Characteristics of Nerve Growth Factor Receptors on PC12 Cells" *J. Biol. Chem.* (1985) vol. 260, pp. 655–662.

Hutton, et al. "Expression of p75$^{NGFR}$ TrkA and TrkB, mRNA in Rat C6 Glioma and Type I Astrocyte Cultures" *J. of Neurosciences Research* (1992), vol. 32, pp. 375–383.

Jing, et al. "Nerve Growth Factor Mediates Signal Transduction Through trk Homodimer Receptors" *Neuron.* (1992) vol. 9, pp. 1067–1079.

Johnson, et al. "Expression and Structure of the Human NGF Receptor" *Cell* (1986) vol. 47, pp. 545–554.

Kaplan, et al. "The trk Proto–Oncogene Product: A Signal Transducing Receptor for Nerve Growth Factor" *Science* (1991) vol. 252, pp. 554–558.

Kaplan, et al. "Tyrosine Phosphorylation and Tyrosine Kinase Activity of the trk Proto–oncogene Product Induced by NGF" *Nature* (1991) vol. 350, pp. 158–160.

Klein, et al. "trkB, A Novel Tyrosine Protein Kinase Receptor Expressed During Mouse Neural Development" *Embro. J.* (1989) vol. 8(12), pp. 3701–3709.

Klein, et al. "The trk Proto–oncogene Encoes a Receptor for Nerve Growth Factor" *Cell* (1991) vol. 65. pp. 189–197.

Knusel, et al. "K–252 Compounds: Modulators of Neurotrophin Signal Transduction" *J. of Neurochemistry* (1992) vol. 59, pp. 187.

Korsching, S. "The Neurotrophic Factor Concept: A Reexamination" *Neorosci.* (1993) vol. 13, pp. 2739–2748.

Lamballe, et al. "trkC, A New Member of the trk Family of Tyrosine Protein Kinases, is a Receptor for Neurotrophin–3" *Cell* (1991) vol. 66, pp. 967–979.

Levi–Montalcini, R. "The Nerve Growth Factor 35 Years Later" *Science* (1987) vol. 237, pp. 1154–1162.

Loeb, et al. "NGF and Other Growth Factors Induce an Association Between ERK1 and the NGF Receptor, gp140$^{prototrk}$" *Neuron* (1992) vol. 9, pp. 1053–1065.

Martin–Zanca, et al. "Molecular and Biochemical Characterization of the Human trk Proto–Oncogene" *Mol. Cell. Biol.* (1989) vol. 9, pp. 24–33.

Martin–Zanca, et al. "Expression of the trk Proto–Oncogene is Restricted to the Sensory Cranial and Spinal Ganglia of Neural Crest Origin in Mouse Development" *Genes Dev.* (1990) vol. 4, pp. 683–694.

Meakin, et al. "Molecular Investigations on the High–Affinity Nerve Growth Factor Receptor" *Neuron* (1991) vol. 6, pp. 153–163.

Middlemas, et al. "trkB, a Neural Receptor Protein–Tyrsoine Kinase: Evidence for a Full–Length and Two Truncated Receptors" *Mol. Cell. Biol.* (1991) vol. 11, pp. 143–143.

Obermeirer, et al. "Tyrosine 785 is a Major Determinant of Trk–Substrate Interaction" *Ebmbro. J.* (1993) vol. 12, pp. 933–941.

Ohmichi, et al. "Nerve Growth Factor Binds to the 140 kd trk Proto–Oncogene Product and Stimulates its Association with the src Homology Domain of Phospholipase C y1" *Biochem. Biophys. Res. Commun.* (1991) vol. 179, pp. 217–223.

Ohmichi, et al. "Activation of Phosphatidylinositol–3 by Nerve Growth Factor Involves Indirect Coupling of the trk Proto–Oncogene with src Homology 2 Domains" *Neuron* (1992) vol. 9, pp. 769–777.

Persson, et al. "Role and Expression of Neurotrophins and the trk Family of Tyrosine Kinase Receptors in Neural Growth and Rescue After Injury" *Current Opinion in Neurology and Neurosurgery* (1993) vol. 6, p. 11.

Pulido, et al. "Dtrk, A Drosophila Gene Related to the trk Family of Neurotrophin Receptors, Encodes A Novel Class of Neural Cell Adhesion Molecule" *Ebro* (1992) vol. 11, pp. 391–404.

Radeke, et al. "Gene Transfer and Molecular Cloning of the Rat Nerve Growth Factor Receptor" *Nature* (1987) vol. 325, 593–597.

Radeke, et al. "Analytical Purification of the Slow, High Affinity NGF Receptor: Identification of a Novel 135 kd Polypeptide" *Neuron* (1991) vol. 7, pp. 141–150.

Ringden, et al. "Mitogenic Properties of Fab and $F(ab')_2$ Fragments of Rabbit Anti–Human $\beta_2$–Microglobulin for Human Lymphocytes" *J. Immunol.* (1977) vol. 6, pp. 281–289.

Schechter, et al. "Novel Roles for Neurotrophins are Suggested by BDNF and NT–3 mRNA Expression in Developing Neurons" *Cells* (1981) vol. 24, pp. 867–874.

Schecterson, et al. "Novel Roles for Neurotrophins are Suggested by BDNF and NT–3 mRNA Expression in Developing Neurons" *Neuron* (1992) vol. 9, pp. 449–463.

Schneider, et al. "A Novel Molecular Mosaic of Cell Adhesion Motifs in the Extracellular Domains of the Neurogenic trk and trkB Tyrosine Kinase Receptors" Oncogene (1991) vol. 6, pp. 1807–1811.

Schodin, et al. "Binding Affinity and Inhibitory Properties of a Single–Chain Anti–T Cell Receptor Antibody" *The J. of Biological Chemistry* (Dec. 1993) vol. 268(34), pp. 25722–25727.

Steele–Perkins, et al. "Insulin–mimetic Anti–insulin Receptor Monoclonal Antibodies Stimulate Receptor Kinase Activity in Intact Cells" *J. Biol. Chem.* (Jun. 1990) vol. 265(16), pp. 9458–9463.

Sutter, et al. "Nerve Growth Factor Receptors" *J. Biol. Chem.* (1979) vol. 254, pp. 5972–5982.

Vetter, et al. "Nerve Growth Factor Rapidly Stimulates Tyrosine Phosphorylation Phospholipase C–y1 by a Kinase Activity Associated with the Product of the trk Proto–oncogene" *Proc. Natl. Acad. Sci. USA* (1991) vol. 88, pp. 5650–5654.

Weskamp, et al. "Evidence that Biological Activity of NGF is Mediated Through a Novel Subclass of High Affinity Receptors" *Neuron.* (1991) vol. 6, pp. 649–663.

Wheeler, et al. J. "Spatiotemporal Patterns of Expression of NGF and the Low–Affinity NGF Receptor in Rat Embryos Suggest Functional Roles in Tissue Morphogenesis and Myogenesis" *Neurosci.* (1992) vol. 12, pp. 930–945.

Wyatt, et al. "Expression of the NGF Receptor Gene in Sensory Neurons and Their Cutaneous Targets Prior to and During Innervation" *Neuron.* (1990) vol. 4, pp. 421–427.

Xie. et al. "Direct Demonstration of MuSK Involvement in Acetylcholine Receptor Clustering Through Identification of Agonist ScFv" *Nature Biotechnology* (Aug. 1997) vol. 15, pp. 768–771.

SEQUENCE LISTING (1) GENERAL INFORMATION:

(iii) NUMBER OF SEQUENCES: 6

(2) INFORMATION FOR SEQ ID NO: 1:

(i) SEQUENCE CHARACTERISTICS:
(A) LENGTH: 26 amino acids
(B) TYPE: amino acid
(D) TOPOLOGY: unknown (ii) MOLECULE TYPE: protein (xi) SEQUENCE DESCRIPTION: SEQ ID NO: 1:

```
Cys Ser Val Leu Asn Glu Thr Ser Phe Ile Phe Thr Gln Phe Leu Glu
1               5                   10                  15

Ser Ala Leu Thr Asn Glu Thr Met Arg His
            20                  25
```

(2) INFORMATION FOR SEQ ID NO: 2:

(i) SEQUENCE CHARACTERISTICS:
(A) LENGTH: 19 amino acids
(B) TYPE: amino acid
(D) TOPOLOGY: unknown (ii) MOLECULE TYPE: protein (xi) SEQUENCE DESCRIPTION: SEQ ID NO: 2:

```
Cys Ala Arg Leu Gln Ala Leu Ala Gln Ala Pro Pro Ser Tyr Leu Asp
1               5                   10                  15

Val Leu Gly
```

(2) INFORMATION FOR SEQ ID NO: 3:

(i) SEQUENCE CHARACTERISTICS:
(A) LENGTH: 36 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO: 3:

```
GGCCGAATTC GCCCGGCGCA GAGAACCTGA CTGAGC                                 36
```

(2) INFORMATION FOR SEQ ID NO: 4:

(i) SEQUENCE CHARACTERISTICS:
(A) LENGTH: 36 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO: 4:

```
GGCCGAATTC ATGTGCTGTT AGTGTCAGGG ATGGGG                                 36
```

(2) INFORMATION FOR SEQ ID NO: 5:

(i) SEQUENCE CHARACTERISTICS:
(A) LENGTH: 40 base pairs
(B) TYPE: nucleic acid
(C) STRANDEDNESS: single -continued

```
        (D) TOPOLOGY: linear

   (ii) MOLECULE TYPE: DNA (genomic)

   (xi) SEQUENCE DESCRIPTION: SEQ ID NO: 5:

CCGAATTCCA TGGCGCGAGG CCAGCGGCAC GGGCAGCTGG                    40


(2) INFORMATION FOR SEQ ID NO: 6:

    (i) SEQUENCE CHARACTERISTICS:
        (A) LENGTH: 45 base pairs
        (B) TYPE: nucleic acid
        (C) STRANDEDNESS: single
        (D) TOPOLOGY: linear

   (ii) MOLECULE TYPE: DNA (genomic)

   (xi) SEQUENCE DESCRIPTION: SEQ ID NO: 6:

CCGAATTCCA TGGCTATTAT TCGTCCTTCT TCTCCACTGG GTCTC              45
```

ANTIBODIES THAT MIMIC ACTIONS OF NEUROTROPHINS

This application is a continuation of 09/033,313, filed Mar. 2, 1998, now abandoned, which is a continuation of 08/466,839, filed Jun. 6, 1995, now abandoned, which is a continuation of 08/162,597, filed Dec. 3, 1993, now U.S. Pat. No. 5,753,225.

This invention was made with Government support under Grant No. MH 28300, awarded by the National Institutes of Health. The Government has certain rights in this invention.

FIELD OF THE INVENTION

This invention relates to the use and production of immunoglobulins which activate trk neurotrophin receptors.

BACKGROUND OF THE INVENTION

The neurotrophins are a family of small, homodimeric proteins which promote effects on distinct but partially overlapping sets of neurons (Levi-Montalcini, R., *Science* 237:1154–62 (1987); Barde, Y. A., *Neuron.* 2:1525–1534 (1989); Korsching, S., *J. Neurosci.* 13:2739–2748 (1993); Eide, F. F., Lowenstein, D. H. and Reichardt, L. F., *Exp. Neurol.* 121:200–214 (1993). For instance, nerve growth factor (NGF), a well characterized member of the neurotrophin family, functions as a target-derived molecule which aids in determining the level of innervation during development by regulating the survival and differentiation, including process outgrowth, of the innervating neuronal population. NGF has effects on apoptosis (programmed cell death) and influences many facets of neuronal development; for example, regulation of axon branching and of gene expression (Barde, 1989).

In addition to NGF, some other members of the neurotrophin family include brain-derived neurotrophic factor (BDNF), neurotrophin-3 (NT-3), and neurotrophin-4/5 (NT-4/5). These various growth factors show selectivity with some overlap as to their responsive neurons in the peripheral nervous system (PNS) and central nervous system (CNS). For instance, neurons responsive to NGF include sympathetic neurons and neural crest sensory neurons in the PNS and basal forebrain cholinergic neurons, striatal cholinergic neurons and cerebellar Purkinje cells in the CNS. PNS neurons responsive to BDNF include placode-derived sensory neurons, neural crest sensory neurons, nodose ganglion neurons and spinal motoneurons. BDNF responsive neurons in the CNS include basal forebrain cholinergic neurons, proprioceptive trigeminal neurons, substantia nigra dopaminergic neurons, retinal ganglion neurons and facial motoneurons. NT-3 responsive neurons include sympathetic and sensory neurons in the PNS and basal forebrain cholinergic neurons and locus coeruleus neurons in the CNS. NT-4/5 responsive neurons in the PNS include sympathetic neurons, dorsal root ganglion neurons and nodose ganglion neurons. NT-4/5 CNS responsive neurons include basal forebrain cholinergic neurons and locus coeruleus neurons.

Redundancy of the neurotrophins and their receptors exists. For instance, trkA receptors bind the neurotrophins NGF, NT-3 and NT-4/5. The receptor trkb binds the neurotrophins BDNF, NT-3 and NT-4/5. The receptor trkC binds NT-3. Although neurotrophins often recognize more than one receptor, they may activate different receptors to different degrees. For example, NT-3 activates trkA moderately, and trkB and trkc strongly.

Neurotrophins are of interest as potential therapeutic agents for a variety of neurodegenerative and neurologic diseases. There are a number of disorders which may relate to suboptimal activity of trk receptors or which are associated with inappropriate activity or levels of neurotrophins. These neurologic disorders include Alzeimer's Disease, Parkinson's Disease, amyotrophic lateral sclerosis (ALS), cerebral ischemia, nerve tissue ischemia, peripheral neuropathy (especially toxic and diabetic peripheral neuropathies), nervous system cancer and epilepsy. Alzeimer's Disease, Parkinson's Disease, ALS, the ischemias, and the neuropathies can be broadly be classified as neurodegenerative disorders.

Parkinson's Disease is also known as paralysis agitans and shaking palsy. It is a chronic, progressive central nervous system disorder characterized by muscular rigidity, tremors and slow purposeful movement as well as a decrease in purposeful movement. Classical Parkinson's Disease is of unknown ideology. However, a Parkinson's syndrome can be drug-induced or caused by poisonings, such as carbon monoxide poisoning, and also by infarction or death of cells in the vicinity of the basal ganglia. Such cell death can be caused by insufficient blood flow, tumors and head trauma. Additionally, a postencephalitic Parkinsonism is known. Parkinson's Disease tends to have insidious onset and a slowly progressive course. It tends to become incapacitating after a number of years.

An additional group of neurogenic disorders includes ALS which is an example of a neurogenic muscular atrophy. Other examples are infantile and juvenile spinal muscular atrophy which, like ALS, are anterior horn cell degenerative diseases. ALS is also know as Lou Gherrig's Disease and includes progressive spinal-muscular atrophy and progressive bulbar palsy. In ALS, muscular weakness and atrophy typically begin in the hands and spread to the forearms and the legs. Muscles fasiculations progressing to spasticity, increased tendon reflexes and extensor plantar reflexes are also characteristic. The afflicted individual generally dies within several years, typically surviving no more than five years. Variants of ALS include progressive spinal-muscular atrophy or Aran-Duchenne muscular atrophy and progressive bulbar palsy or Duchenne's paralysis or labioglossolaryngeal paralysis.

Peripheral neuropathies and peripheral neuritis include a large group of sensory, motor, reflex and vaso-motor symptoms which may be single or in combination and which may be produced by disease of a single nerve (mononeuropathy), or two or more nerves in separate areas (mononeuritis multiplex), or many nerves simultaneously (polyneuropathy, polyneuritis, multiple peripheral neuritis or multiple peripheral neuropathy). The etiologies include collagen vascular conditions, infections, toxic agents, malignancies, metabolic and autoimmune causes. For example, a toxic peripheral neuropathy can be caused by the chemotherapeutic agent taxol which can disrupt axonal transport in peripheral neurons. This causes pain in the nerve distribution of the afflicted neurons. Diabetic neuropathy is another example of a peripheral neuropathy. In diabetic neuropathy, peripheral sensory and sympathetic neurons tend to be affected early in the course of the disease usually causing pain or decreased sensation.

Epilepsy or seizure disorder includes a variety of seizures characterized by recurrent paroxysmal cerebral dysfunction associated with sudden, usually brief, attacks of altered consciousness, motor activity, sensory phenomena or inappropriate behavior. Any recurrent seizure pattern can be called epilepsy. Convulsive seizures are probably the most common form of attack and they begin with loss of consciousness and loss of motor control followed by tonic or clonic jerking of the extremities. In about three quarters of seizure cases in adults, no clear etiology is identified and the seizure is termed "symptomatic" or "idiopathic." Some of the known causes of seizures include cerebral trauma, tumors or other brain disease, CNS infections, hyperpyrexia such as that associated with acute infection or heat stroke, toxic agents, metabolic disturbances, cerebral infarction or hemorrhage, cerebral hypoxia and a variety of other causes. Drug therapy with anticonvulsive agents is frequently effective.

There has been some exploration of the possibility of using neurotrophins to treat disease. For example, in animal models of both taxol toxic and diabetic peripheral neuropathies, NGF was used as a therapy with varying degrees of success. See Eide, et al. at page 206. However, because of the redundancy of neurotrophin-receptor recognition and because of variability in the strength of activation of their corresponding receptors, neurotrophins present complex problems as potential therapeutic agents. Additionally, several physiologic mechanisms exist for rapidly clearly neurotrophins from the circulation, including the presence of receptor-like binding proteins whose main function may be to sequester the neurotrophins. Additionally neurotrophins are difficult to prepare in quantity because of complex requirements for post-translational processing and their lability to proteases.

The importance of the neurotrophins has stimulated interest in their receptors and signal transduction mechanisms. Most approaches have focused on the pheochromocytoma cell line PC12, which is transformed into a sympathetic neuron-like cell when exposed to NGF (Greene, L. A. and Tischler, A., *Proc. Natl. Acad. Sci. USA* 73:2424–2428 (1976)). NGF binding studies indicated that NGF could bind to at least two different sites, a low affinity or fast-dissociating binding site, and a high affinity or slow-dissociating binding site (Sutter, et al., *J. Biol. Chem.* 254:5972–5982 (1979); Schechter, A. L. and Bothwell, M. A., *Cell.*, 24, 867–874 (1981)).

A receptor for NGF, known as the low affinity nerve growth factor receptor (LNGFR), has been cloned from rat and human sources (Radeke, et al., 325:593–7 (1987); Johnson, et al., *Cell.* 47:545–554 (1986)). It is a transmembrane glycoprotein of 75,000 daltons, and it is expressed in many neuronal and nonneuronal cell types (Wyatt, et al., *Neuron.* 4:421–7 (1990); Wheeler, E. F. and Bothwell, M., *J. Neurosci.* 12:930–45 (1992)). However, LNGFR was unable to bind NGF with a high affinity in transfected fibroblastic cell lines (Radeke, et al., 1987).

Crosslinking studies (Hosang, M. and Shooter, E. M., *J. Biol. Chem.* 260:655–662 (1985)), biochemical characterization (Meakin, S. O. and Shooter, E. M., *Neuron.* 6:153–163 (1991); Radeke, M. J. and Feinstein, S. C., *Neuron.* 7:141–50 (1991)), and binding and culture studies with the anti-LNGFR polyclonal antibody REX (Weskamp, G. and Reichardt, L. F., *Neuron.* 6:649–63 (1991)) implied that another receptor for NGF is expressed by PC12 cells. That receptor has since been identified as the receptor tyrosine kinase $p140^{trk}$ or trkA (Kaplan, et al., *Science.* 252:554–8 (1991); Klein, et al., *Cell.* 65:189–97 (1991)).

TrkA is expressed in sensory and sympathetic neurons in the peripheral nervous system, and basal forebrain neurons in the central nervous system, all cell types which show responses to NGF (Martin-Zanca, et al., *Genes Dev.* 4:683–94 (1990); Schecterson, L. C. and Bothwell, M., *Neuron.* 9:449–63 (1992); Holtzman, et al., *Neuron.* 9:465–78 (1992)). Biochemical studies have demonstrated that trkA is phosphorylated in response to NGF (Kaplan, et al., *Nature* 350:158–60 (1991); Klein, et al., (1991); Jing, et al., *Neuron.* 9:1067–79 (1992)), and subsequently trkA activates several signal transduction pathways (Vetter, et al., *Proc. Natl. Acad. Sci. USA* 88:5650–4 (1991); Loeb, et al., *Neuron.* 9:1053–65 (1992); Obermeier, et al., *Embo. J.* 12:933–941 (1993)).

TrkB and trkC, two receptors closely related to trkA, have been isolated and can respond to other members of the neurotrophin family (Martin-Zanca, et al., *Mol. Cell. Biol.* 9:24–33 (1989); Klein, R., et al., *Embo. J.* 8:3701–9 (1989); Middlemas, et al., *Mol. Cell. Biol.* 11:143–53 (1991); Lamballe, et al., (1991)).

SUMMARY OF THE INVENTION

The invention relates to the discovery that selected immunoglobulins can activate trk receptors and mimic the actions of neurotrophins. Included in the invention are methods for activating a trk receptor comprising exposing cells having the trk receptor to a multivalent immunoglobulin which binds to the receptor and activates the receptor. The trk receptor is any of a number of tyrosine kinase receptors, and preferably it is any of trkA, trkB, and trkC.

Activation of the receptor can be noted by a variety of means including increased phosphorylation of the receptor, increased phosphorylation of protein substrates that are phosphorylated in response to activation of the receptor, and promotion of the effector function or outcome of receptor activation. Examples of such functions or outcomes include promotion of neuronal survival and promotion of neuronal differentiation including neurite outgrowth.

The multivalent immunoglobulin is preferably bivalent, although it can be polyvalent. Typically the immunoglobulin is a monoclonal antibody.

The invention includes methods of therapy for neurologic disorders associated with suboptimal activity of a trk receptor. Such disorders include Alzheimer's disease, Parkinson's disease, amyotrophic lateral sclerosis (ALS), cerebral ischemia, nerve tissue ischemia, peripheral neuropathy, particularly toxic and diabetic peripheral neuropathy, nervous system cancer, and epilepsy. Examples of nervous system cancer are primitive neuroectodermal tumors, neuroblastomas, medulloblastomas, ganglioneuromas, Ewing's sarcoma, gliomas, glioblastomas, and astrocytomas.

The therapeutic method includes administering to a mammal having the disorder a therapeutically effective amount of a multivalent immunoglobulin of the invention. Usually the mammal is a human, although veterinary use is also contemplated. The administration is preferably parenteral, especially intraventricular, intravenous or intramuscular. The effective amount is an amount sufficient to cause a desired effect such as a therapeutic benefit. Typically, the dosage is selected from the range of from about 1 $\mu$g/kg to about 1 mg/kg body weight of the recipient mammal for a polyclonal antibody. The range for a monoclonal antibody is usually about 5% to about 10% of the polyclonal antibody range.

A method for diagnosing a neurologic disorder associated with suboptimal activity of a trk receptor is also supplied. The method includes obtaining a nerve cellular sample, exposing the sample to a multivalent immunoglobulin which (1) binds to the receptor and (2) activates the receptor, and assaying the sample for (1) binding to the immunoglobulin and (2) activation of the receptor.

Also provided is a method for determining whether cellular material has a trk receptor. This method includes exposing the cellular material to a multivalent immunoglobulin which both binds to and activates the receptor and assaying the cellular material for binding to the immunoglobulin and activation of the receptor.

Thus, the invention provides immunoglobulins that mimic the actions of neurotrophins. Appropriately designed immunoglobulins able to dimerize the neurotrophin-receptors can activate these receptors and serve as neuronal survival and differentiation-promoting agents. Such immunoglobulins are easier to prepare, are more stable, and are likely to be longer acting than neurotrophins. In some cases immunoglobulins can be designed to act with greater selectivity than certain neurotrophins, several of which recognize more than one receptor. Bifunctional organic molecules that bind neurotrophin receptors are likely to also activate these receptors.

Immunoglobulins able to bind and cross-link the trk family of neurotrophin-receptors are shown herein to activate these receptors and produce consequences in neurons indistinguishable from exposure to a neurotrophin. Bivalent or polyvalent antibodies or immunoglobulins are required. Observed activation sequelae include tyrosine phosphorylation of the trk-receptor, tyrosine phosphorylation of the protein substrates that are phosphorylated as a response to the neurotrophin, promotion of neuronal survival, and promotion of neuronal differentiation including neurite outgrowth. Thus, the immunoglobulins mimic the actions of the neurotrophins.

Also provided are immunoglobulins, and methods of use, which are monovalent and which bind to and prevent activation of trk receptors. Such immunoglobulins and methods block the relevant receptor and prevent the receptor's effect or function from occurring.

Immunoglobulins can be designed to recognize only single receptors. Included herein are data supporting detection of differentially spliced exons encoding extracellular domains in trk. Immunoglobulins recognizing specific receptor isoforms can be prepared. Immunoglobulins have different, and in some cases more restricted, specificities that are useful for targeting the therapy.

Immunoglobulins, especially monoclonal antibodies, are easy to prepare and purify. They can be designed to eliminate problems of antigenic responses or complement activation. They have considerable therapeutic potential in general. Additionally, they may be more efficiently delivered to neurons than are neurotrophins. Immunoglobulins would not be cleared as rapidly by their respective receptors and they are comparatively easy to prepare and purify. Also they are resistant to most proteases.

DETAILED DESCRIPTION

Figure 1A:
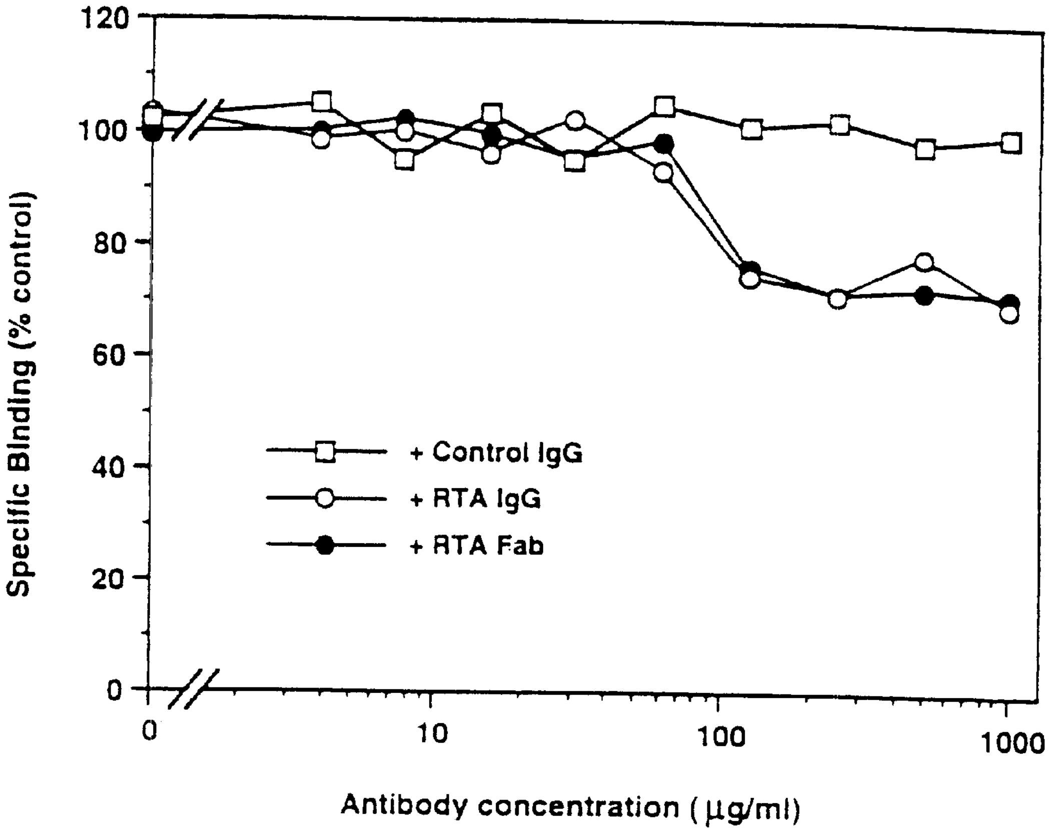
FIG. 1A is a dose response graph of a whole cell binding assay with antibodies of the invention.

This invention provides immunoglobulin peptides which bind to and activate trk receptors and methods of use. Additionally, monovalent immunoglobulin peptides which bind to and block activation of trk receptors and methods of use are provided.

The term "tyrosine kinase" refers to a family of enzymes which possess in common the ability to phosphorylate (add a phosphate group to) the amino acid tyrosine. The tyrosine kinases are tightly regulated in animal cells. One fairly well characterized tyrosine kinase is epidermal growth factor receptor which assists in initiating cell division by phosphorylating key proteins. For information about the protein kinase families and hallmarks of each family, see generally Hanks, et al. *Science* 241:42–52 (1988), incorporated by reference herein.

The neurotrophins bind to appropriate tyrosine kinase receptors. Several features are considered hallmarks of the trk tyrosine kinase receptor family. For example, see Klein, et al. *EMBO* 8(12) 3701–3709 (1989) and Schneider, R. and M. Schweiger, *Oncogene* 6:1807–1811 (1991), both of which are incorporated by reference herein. Specifically, four features unique to the trk receptor family have been identified and include (1) a single amino acid gap between residues 575 and 576 in mouse trkB, residues 542 and 543 in human trkA; (2) a threonine in position 678 in mouse trkB, position 647 in human trkA; (3) a tryptophan in position 753 in trkB, position 722 in human trkA; and (4) the absence of the helix-breaking proline in position 797 in trkB, position 766 in human trkA.

Relating to preferred embodiments, three closely related tyrosine kinase receptors are known currently: trkA, trkB and trkC. The trk receptor proteins include an extracellular domain for ligand recognition, a single transmembrane domain and a cytoplasmic tail which contains the tyrosine kinase. The cytoplasmic tail initiates the signalling cascade. The extracellular domain has two immunoglobulin-like domains that bind neurotrophins. The actual process or mechanism of activation is not clear, but it is thought that the receptors are activated by allosteric dimerization such that the tyrosine kinase receptors form oligomers in response to binding by an appropriate growth factor. The receptor identified as the receptor tyrosine kinase $p140^{trk}$ or trkA is described in Kaplan, et al., *Science.* 252:554–8 (1991) and Klein, et al., *Cell.* 65:189–97 (1991), both incorporated by reference herein.

TrkA is expressed in sensory and sympathetic neurons in the peripheral nervous system, and basal forebrain neurons in the central nervous system, all cell types which show responses to NGF (Martin-Zanca, et al., *Genes Dev.* 4:683–94 (1990); Schecterson, L. C. and Bothwell, M., *Neuron.* 9:449–63 (1992); Holtzman, et al., *Neuron.* 9:465–78 (1992), all incorporated by reference herein). Biochemical studies have demonstrated that trkA is phosphorylated in response to NGF (Kaplan, et al., *Nature* 350:158–60 (1991); Klein, et al., (1991); Jing, et al., *Neuron.* 9:1067–79 (1992), all incorporated by reference herein), and subsequently trkA activates several signal transduction pathways (Vetter, et al., *Proc. Natl. Acad. Sci. USA* 88:5650–4 (1991); Loeb, et al., *Neuron.* 9:1053–65 (1992); Obermeier, et al., *Embo. J.* 12:933–941 (1993), all incorporated by reference herein).

TrkB and trkC, two receptors closely related to trkA, have been isolated and can respond to other members of the neurotrophin family (Martin-Zanca, et al., *Mol. Cell. Biol.* 9:24–33 (1989); Klein, R., et al., *Embo. J.* 8:3701–9 (1989); Middlemas, et al., *Mol. Cell. Biol.* 11:143–53 (1991); Lamballe, et al., (1991), all incorporated by reference herein).

Immunoglobulins or antibodies are typically composed of four covalently bound peptide chains. For example, an IgG antibody has two light chains and two heavy chains. Each light chain is covalently bound to a heavy chain. In turn each heavy chain is covalently linked to the other to form a "Y" configuration, also known as an immunoglobulin conformation. Fragments of these molecules, or even heavy or light chains alone, may bind antigen. Antibodies, fragments of antibodies, and individual chains are also referred to herein as immunoglobulins.

A normal antibody heavy or light chain has an N-terminal ($NH_2$) variable (V) region, and a C-terminal (—COOH) constant (C) region. The heavy chain variable region is referred to as $V_H$ (including, for example, $V_\gamma$), and the light chain variable region is referred to as $V_L$ (including $V_\kappa$ or $V_\lambda$). The variable region is the part of the molecule that binds to the antibody's cognate antigen, while the Fc region (the second and third domains of the C region) determines the antibody's effector function (e.g., complement fixation, opsonization).

An immunoglobulin light or heavy chain variable region consists of a "framework" region interrupted by three hypervariable regions, also called complementarity-determining regions or CDRs. The extent of the framework region and CDRs have been defined (see, "Sequences of Proteins of Immunological Interest," E. Kabat, et al., U.S. Department of Health and Human Services, (1987); which is incorporated herein by reference). The sequences of the framework regions of different light or heavy chains are relatively conserved within a species. The framework region of an antibody, that is the combined framework regions of the constituent light and heavy chains, serves to position and align the CDRs in three dimensional space. The CDRs are primarily responsible for binding to an epitope of an antigen. The CDRs are typically referred to as CDR1, CDR2, and CDR3, numbered sequentially starting from the N-terminus.

The two types of light chains, κ and λ, are referred to as isotypes. Isotypic determinants typically reside in the constant region of the light chain, also referred to as the $C_L$ in general, and $C_\kappa$ or $C_\lambda$ in particular. Likewise, the constant region of the heavy chain molecule, also known as $C_H$, determines the isotype of the antibody. Antibodies are referred to as IgM, IgD, IgG, IgA, and IgE depending on the heavy chain isotype. The isotypes are encoded in the mu (μ), delta (Δ), gamma (γ), alpha (α), and epsilon (ϵ) segments of the heavy chain constant region, respectively. In addition, there are a number of γ subtypes.

Immunoglobulins are frequently classified according to their valency. IgG is a bivalent antibody and IgM is a polyvalent antibody. The valency refers to the number of binding sites on the immunoglobulin. As used herein, the term multivalent means that one antibody molecule binds two or more receptors. Bivalent means that the antibody binds to two receptors and polyvalent means that it binds to more than two receptors. Polyclonal antibodies generally comprise a mixture of bivalent antibodies. Methods of the invention relating to activation of a trk receptor include the use of bivalent and polyvalent immunoglobulins (that is, multivalent but not monovalent immunoglobulins). In preferred embodiments a single bivalent monoclonal antibody or a mixture of bivalent antibodies, such as monoclonal antibodies, is used. More preferably, the immunoglobulins can include a mixture of at least two monoclonal antibodies.

The heavy chain isotypes determine different effector functions of the antibody. In addition, the heavy chain isotype determines the secreted form of the antibody. Secreted IgG, IgD, and IgE isotypes are typically found in single unit or monomeric form. Secreted IgM isotype is found in pentameric form; secreted IgA can be found in both monomeric and dimeric form.

Mouse monoclonal antibodies have been described against the extracellular portion of trk. See, for example, Eager, K., *Onc.* 6(5):819–824 (May 1991) and EPA No. 91112109 (Pub. No. 0471205A1).

Murine, human, chimeric or other immunoglobulins, especially those of mammalian origin, may be used with the invention. The immunoglobulins can be prepared in a variety of ways known in the art, depending upon whether monoclonal or polyclonal antibodies are desired. For polyclonal antibodies, a vertebrate, typically a domestic animal, is hyperimmunized with the antigen, blood from the vertebrate is collected shortly after immunization and the gamma globulin is isolated. Suitable methods for preparing polyclonal antibodies are described in the *Handbook of Experimental Immunology,* 3d ed., Weir (ed.), Blackwell Scientific Publications (1978).

For monoclonal antibodies, a small animal, typically a rat or mouse, is hyperimmunized with antigen, the spleen is removed and the lymphocytes are fused with myeloma cells in the presence of a suitable fusion promoter. The resulting hybrid cells or hybridomas are screened to isolate individual clones, each of which secrete a single antibody species to the antigen. The individual antibody species are each the product of a single B cell generated in response to a specific antigenic site recognized on the antigen or immunogenic substance. The process for obtaining monoclonal antibodies is described by Kohler and Milstein, *Nature,* 256:495 (1975). See also Harlow and Lane, *Antibodies: A Laboratory Manual,* Cold Spring Harbor Publications, N.Y. (1988). The peptides or antigens used to generate the antibodies, depending upon their own immunogenicity, may be used directly in the immunization procedure as immunogenic components associated with living or fixed cells or they may be bound to a suitable carrier protein, such as keyhole limpet hemocyanin (KLH), human or bovine serum albumin (HSA or BSA), and the like. Use of the antigen with a carrier protein is preferred.

The DNA sequences associated with this invention comprise DNA subsequences encoding amino acid sequences of the antibody heavy or light chains, or fragments thereof, which determine binding specificity for a trk receptor protein such as those derived from trkA. These sequences may be ligated, for example, into human constant region expression vectors, and inserted into a host cell. The host cell can then express a recombinant chimeric or hybrid antibody that is specific for binding to a trk receptor protein or polypeptide.

"Immunoglobulin" or "antibody peptide(s)" refers to an entire immunoglobulin or antibody or any functional fragment of an immunoglobulin molecule. Examples of such peptides include complete antibody molecules, antibody fragments, such as Fab, $F(ab')_2$, CDRS, $V_L$, $V_H$, and any other portion of an antibody. As described above, an IgG antibody molecule is composed of two light chains linked by disulfide bonds to two heavy chains. The two heavy chains are, in turn, linked to one another by disulfide bonds in an area known as the hinge region of the antibody. A single IgG molecule typically has a molecular weight of approximately 150–160 kD and containing two antigen binding sites.

An $F(ab')_2$ fragment lacks the C-terminal portion of the heavy chain constant region, and has a molecular weight of approximately 110 kD. It retains the two antigen binding sites and the interchain disulfide bonds in the hinge region, but it does not have the effector functions of an intact IgG molecule. An $F(ab')_2$ fragment may be obtained from an IgG molecule by proteolytic digestion with pepsin at pH 3.0–3.5 using standard methods such as those described in Harlow and Lane, supra.

The use of high concentrations of mouse antibodies (or other nonhuman antibodies) in humans has certain limitations. There are instances of anti-framework or anti-idiotype antibodies generation over the course of longterm therapy. Therefore, chimeric antibodies may also be used in the combination of this invention, which can minimize an antimurine response. Chimeric antibodies are usually combinations of portions of human and murine antibodies with the variable region of the murine line combined with the invariant or constant region of the human line. An example of a successful human/murine chimeric antibody is one for carcinoembryonic (CEA) antigen described by Beidler, et al., *J. of Immunology,* 141:4053 (1988). Other methods for constructing chimeric antibodies and binding fragments are described in Brown et al., *Cancer Research* 47:3577–3583 (1987); Kameyama et al., *FEB* 2:301–306 (1989); Orlandi et al., *Proc. Nat'l Acad. Sci. USA* 86:3833–3837 (1989); Beidler et al., *J. Immun.* 141:4053 (1986); Sahagan et al., *J. Immunol.* 3:1066 (1986); Bird et al., *Science* 242:123 (1988); Morrison et al., *Clin. Chem.* 34:1668–1675 (1988); Better et al., *Science* 240:1041 (1988) and Morrison and Oi, *Advances in Immunology* 44:55 (1989) all of which are incorporated by reference herein.

"Chimeric antibodies" or "chimeric peptides" refer to those antibodies or antibody peptides wherein one portion of the peptide has an amino acid sequence that is derived from, or is homologous to, a corresponding sequence in an antibody or peptide derived from a first gene source, while the remaining segment of the chain(s) is homologous to corresponding sequences of another gene source. For example, a chimeric antibody peptide may comprise an antibody heavy chain with a murine variable region and a human constant region. The two gene sources will typically involve two species, but will occasionally involve one species.

Chimeric antibodies or peptides are typically produced using recombinant molecular and/or cellular techniques. Typically, chimeric antibodies have variable regions of both light and heavy chains that mimic the variable regions of antibodies derived from one mammalian species, while the constant portions are homologous to the sequences in antibodies derived from a second, different mammalian species.

The definition of chimeric antibody, however, is not limited to this example. A chimeric antibody is any antibody in which either or both of the heavy or light chains are composed of combinations of sequences mimicking the sequences in antibodies of different sources, whether these sources are differing classes, differing antigen responses, or differing species of origin, and whether or not the fusion point is at the variable/constant boundary. For example, chimeric antibodies can include antibodies where the framework and complementarity-determining regions are from different sources. For example, non-human CDRs are integrated into human framework regions linked to a human constant region to make "humanized antibodies." See, for example, PCT Application Publication No. WO 87/02671, U.S. Pat. No. 4,816,567, EP Patent Application 0173494, Jones, et al., *Nature* 321:522–525 (1986) and Verhoeyen, et al., *Science* 239:1534–1536 (1988), all of which are incorporated by reference herein.

A "human-like framework region" is a framework region for each antibody chain, and it usually comprises at least about 70 or more amino acid residues, typically 75 to 85 or more residues. The amino acid residues of the human-like framework region are at least about 80%, preferably about 80 to 85%, and most preferably more than 85% homologous with those in a human immunoglobulin.

The term "humanized" or "human-like immunoglobulin" refers to an immunoglobulin comprising a human-like framework region and a constant region that is substantially homologous to a human immunoglobulin constant region, e.g., having at least about 80% or more, preferably about 85 to 90% or more and most preferably about 95% or more homology. Hence, most parts of a human-like immunoglobulin, except possibly the CDRS, are substantially homologous to corresponding parts of one or more native human immunoglobulin sequences.

"Hybrid antibody" refers to an antibody wherein each chain is separately homologous with reference to a mammalian antibody chain, but the combination represents a novel assembly so that two different antigens are recognized by the antibody. In hybrid antibodies, one heavy and light chain pair is homologous to that found in an antibody raised against one epitope, while the other heavy and light chain pair is homologous to a pair found in an antibody raised against another epitope. This results in the property of multi-functional valency or multivalency, i.e., ability to bind at least two different epitopes simultaneously. Such hybrids may, of course, also be formed using chimeric chains.

The present invention encompasses, inter alia, a chimeric antibody, including a hybrid antibody or a humanized or human-like antibody. It also encompasses a recombinant DNA sequence encoding segments of said antibody or any peptide specific for a trk receptor protein. Variants of these sequences are also included, such as substitution, addition, and/or deletion mutations, or any other sequence possessing substantially similar binding activity to the sequences from which they are derived or otherwise similar to.

For this invention, an immunoglobulin, antibody or other peptide is specific for a trk receptor protein if the immunoglobulin antibody or peptide binds or is capable of binding trk receptor protein as measured or determined by standard antibody-antigen or ligand-receptor assays, for example, competitive assays, saturation assays, or standard immunoassays such as ELISA or RIA. This definition of specificity applies to single heavy and/or light chains, CDRS, fusion proteins or fragments of heavy and/or light chains, that are also specific for trk protein if they bind trk protein alone or if, when properly incorporated into immunoglobulin conformation with complementary variable regions and constant regions as appropriate, are then capable of binding trk protein.

In competition assays the ability of an antibody or peptide fragment to bind an antigen is determined by detecting the ability of the peptide to compete with the binding of a compound known to bind the antigen. Numerous types of competitive assays are known. Alternatively, assays that measure binding of a test compound in the absence of an inhibitor may also be used. For instance, the ability of a molecule or other compound to bind the trk receptor protein can be detected by labelling the molecule of interest directly or it may be unlabelled and detected indirectly using various sandwich assay formats. Numerous types of binding assays such as competitive binding assays are known (see, e.g., U.S. Pat. Nos. 3,376,110, 4,016,043, and Harlow and Lane, supra which are incorporated herein by reference). Assays for measuring binding of a test compound to one component alone rather than using a competition assay are also available. For instance, immunoglobulins can be used to identify the presence of the trk receptor protein. Standard procedures for monoclonal antibody assays, such as ELISA, may be used (see, Harlow and Lane, supra). For a review of various signal producing systems which may be used, see, U.S. Pat. No. 4,391,904, which is incorporated herein by reference.

Further, the specificity of the immunoglobulin peptides can be determined by their affinity for the trk receptor. Such specificity exists if the dissociation constant ($K_D$=1/K, where K is the affinity constant) of the peptides is <1 μM, preferably <100 nM, and most preferably <1 nM. Immunoglobulins typically have a $K_D$ in the lower ranges. $K_D$=[R-L]/[R][L] where [R], [L], and [R-L] are the concentrations at equilibrium of the receptor (R), ligand or peptide (L) and receptor-ligand complex (R-L), respectively. Typically, the binding interactions between ligand or peptide and receptor or antigen include reversible noncovalent associations such as electrostatic attraction, Van der Waals forces and hydrogen bonds.

Other assay formats may involve the detection of the presence or absence of various physiological or chemical changes that result from the interaction, such as down modulation, internalization or an increase in phosphorylation as described in *Receptor-Effector coupling—A Practical Approach,* ed. Hulme, IRL Press, Oxford (1990).

A preferred peptide specific for trk receptor protein induces an increase in the phosphorylation of the trk receptor protein when placed in contact with cells expressing the trk receptor protein. A molecule that induces an increase in the phosphorylation of trk receptor protein is one that causes a detectable increase in the incorporation of phosphate into the protein over that which occurs in the absence of the molecule. Typically this detectable increase will be a two-fold or greater increase in phosphorylation, preferably greater than a three-fold increase over controls. Phosphorylation may be measured by those methods known in the art for detecting phosphorylation of receptors. See, for example Cooper, et al., *Methods in Enzymology* 99:387–402 (1983); Antoniades and Pantazis, *Methods in Enzymology* 147:36–40 (1987); and Lesniak, et al., *Methods in Enzymology* 150:717–723 (1987), which are all incorporated by reference herein.

Typically, phosphorylation can be measured by in vivo phosphorylation of intact cells (Lesniak, supra) or by an in vitro autophosphorylation reaction (Antonaides, supra). For measuring in vivo phosphorylation, for example, assays may be conducted where cells bearing the trk receptor protein are placed into contact with radioactive labelled phosphate. To detect phosphorylation of the trk receptor protein receptor in the in vivo assay, it is advantageous to incubate the test cells for about 12 to about 18 hours, with the labeled phosphate. The cells are divided into two or more batches, where some are exposed to the molecule expected to increase the phosphorylation of the receptor and some are separated out as controls. The aliquots are subsequently immunoprecipitated, the receptor is recognized, for example, by SDS polyacrylamide gel or autoradiography methods, and an increase in phosphorylation is considered statistically significant when there is a two-fold or greater increase in the background of the aliquot exposed to the test molecule over the control aliquots.

To measure in vitro autophosphorylation, for example, cells or cell extracts may be incubated in the presence or absence of the peptide specific for trk receptor. Following immunoprecipitation with an anti-trk receptor antibody, the immune complex may be incubated with $\gamma^{32}$P-ATP and analyzed by SDS-PAGE autoradiography. For methods for demonstrating trk receptors and for phosphate labelling studies, in vitro and in vivo, see *Receptor-Effector Coupling: A Practical Approach,* E. C. Hulme, ed., chapter 8, Oxford Univ. Press (1990), incorporated by reference herein.

Activation of the trk receptor can be evaluated not only by detecting phosphorylation or an increase in phosphorylation, but also by other means. For example, neuron survival counts or differentiation studies, such as dendritic outgrowth, collateral sprouting and axon branching, also indicate that an activation of the trk receptor has occurred. Additionally, the artisan could observe for signs associated with synaptogenesis and changes in the regulation of neurotransmitter synthesis.

Another general method of evaluating for activation of the trk receptor relates to identifying complex formation with signaling substrates. For instance, a trk-phospholipase C complex has been known to form after trk receptor activation. An immunoprecipitation study can detect the phospholipase C associated with the receptor complex. Additionally, it is thought that other proteins exist in complex formation with trk receptor activation and that all of such proteins are not yet fully identified or characterized. The above method of detection of receptor activation can be applied to whole cells, tissue and tumor samples. See, for example, Vetter, et al., *PNAS* 88:5650–5654 (July 1991), incorporated by reference herein.

Another such method which has the advantage of requiring a small amount of tissue involves detecting activation of the trk receptor by identifying certain intermediate-early gene products. These gene products can be evaluated for by RNA analysis or immunohistochemistry and are produced by certain genes which are activated about 30 minutes after trk receptor activation. See Collazo, et al., *Neuron* 9:643–656 (October 1992), incorporated by reference herein. One can evaluate for the presence of these short-lived regulatory proteins in the cell nucleus. The regulatory protein is used as a marker for phosphorylation induction. In this method, a sample such as a tissue slice is prepared and an immunoglobulin of the invention is applied to the tissue slice. Cells which have had their trk receptors activated in response to the immunoglobulin application will have demonstrable intermediate-early gene products (such as fos) in their nucleus. Another antibody which is specific for the protein being used as a marker is then applied to the tissue preparation to allow complex formation. Complex formation is detected by means well known in the art to decide whether trk activation has occurred.

An agonist of a receptor is a substance, such as an immunoglobulin, which activates the receptor. Thus, to identify an agonist, one can evaluate for receptor activation as discussed herein.

In embodiments wherein blocking of a trk receptor is desired, binding of the immunoglobulin to the receptor can be evaluated as described above in the presenece of the preferred neurotrophin ligand, but activation will not occur. Thus, phosphorylation does not increase and evaluations of effect or function (e.g., neuron survival) show no significant enhancement. For instance, a cancer such as a neuroblastoma may grow in response to activation of a trk receptor. Thus, treatment with a monovalent immunoglobulin according to the invention could assist with therapy by slowing or stopping tumor growth by blocking the receptor.

To identify antibodies with the desired specificity a number of well-defined techniques, such as their ability to stain neurons via histochemical means, to react with intact neurons on a Fluorescence-activated cell sorter (FACS), or to react with the purified trk protein in either an immunoprecipitation assay or in a Western blot assay, are known.

Using standard methods that are well known in the art, the variable regions and CDRs may be derived from a hybridoma that produces a monoclonal antibody that is specific for a trk receptor. The nucleic acid sequences of the present invention capable of ultimately expressing the desired chimeric antibodies can be formed from a variety of different nucleotide sequences (genomic or cDNA, RNA, synthetic oligonucleotides, etc.) and components (e.g., V, J, D, and C regions), as well as by a variety of different techniques. Joining appropriate genomic sequences is presently a common method of production, but cDNA sequences may also be utilized (see, European Patent Publication No. 0239400 and Reichmann, L., et al., *Nature,* 332:323–327 (1988), both of which are incorporated herein by reference).

A similar approach can be taken to isolate and subclone the sequences encoding the constant regions of the heavy and light chains that originate from another mammalian species. The enhancers to the heavy and light chain can be included in the isolated heavy chain fragments, or can alternatively be isolated and subcloned.

Human constant region DNA sequences are preferably isolated from immortalized B-cells, see e.g., Heiter, et al., *Cell,* 22:197–207 (1980), incorporated by reference herein, but can be isolated or synthesized from a variety of other sources. The nucleotide sequence of a human immunoglobulin $C_{\gamma 1}$, gene is described in Ellison, et al., *Nucl. Acid. Res.,* 10:4071 (1982); Beidler, et al., *J. Immunol.,* 141:4053 (1988); Liu, et al., *Proc. Natl. Acad. Sci. USA,* 84:3439 (1987) (all incorporated by reference herein).

The CDRs for producing the immunoglobulins of the present invention preferably are derived from monoclonal antibodies capable of binding to the desired antigen, trk receptor protein, and produced in any convenient mammalian source, including, mice, rats, rabbits, hamsters, or other vertebrate host cells capable of producing antibodies by well known methods. Suitable source cells for the DNA sequences and host cells for immunoglobulin expression and secretion can be obtained from a number of sources, such as the American Type Culture Collection ("ATCC") ("Catalogue of Cell Lines and Hybridomas," Fifth edition (1985) Rockville, Md., U.S.A., which is incorporated herein by reference).

In addition to the antibody peptides specifically described herein, other "substantially homologous" modified immunoglobulins can be readily designed and manufactured utilizing various recombinant DNA techniques known to those skilled in the art. Modifications of the genes may be readily accomplished by a variety of well-known techniques, such as site-directed mutagenesis (see, Gillman and Smith, *Gene,* 8:81–97 (1979) and Roberts, S., et al., *Nature,* 328:731–734 (1987), both of which are incorporated herein by reference). Alternatively, polypeptide fragments comprising only a portion of the primary antibody structure may be produced, which fragments possess binding and/or effector activities.

The cloned variable and constant regions can be isolated from plasmids and ligated together into a mammalian expression vector, such as pSV2-neo, and pRSV-gpt, to form a functional transcription unit. These expression vectors can then be transfected into host cells. Mouse myeloma cells, such as SP 2/0 or P3X cells, are a preferred host because they do not secrete endogenous immunoglobulin protein and contain all of the components used in immunoglobulin expression. Myeloma cells can be transfected using appropriate techniques as described above.

Other types of promoters and enhancers specific for other host cells are known in the art. See, Kameyoma, K., et al., supra. For example, the DNA sequence encoding the chimeric antibody amino acid sequence can be linked to yeast promoters and enhancers and transfected into yeast by methods well known in the art. See, Kriegler, supra.

This same approach can be taken to isolate the trk receptor specific CDRs from one source such as one mammalian species and the framework regions of another source, such as a different mammalian species. The CDRs can then be ligated to the framework regions and constant regions to form a chimeric antibody. See, PCT No., GB88/00731 (1989), which is incorporated by reference. The CDRs could be cloned in an expression vector comprising, for example, human framework and constant regions.

Another example is a recombinant DNA sequence comprising the heavy and/or light chain CDR1, CDR2, and CDR3 of one species, such as mouse, and the framework regions of human heavy chain to encode an antibody specific for trk. Other possibilities include using CDRs specific for trk; using part of the variable region encompassing CDR1 and CDR2 from one mammalian species, and then ligating this sequence to another encoding the framework portions of a second mammalian species to the CDR3 of the first; or transfecting a host cell line with a recombinant DNA sequence encoding a trk specific heavy chain CDRs derived from a first mammalian species, interspersed within the framework of a second mammalian species with a light chain containing a variable region DNA sequence derived from the first species and the constant region derived from the second species.

Antibodies may be expressed in an appropriate folded form, including single chain antibodies, from bacteria such as *E. coli.* See, Pluckthun, *Biotechnology,* 9:545 (1991); Huse, et al., *Science,* 246:1275 (1989) and Ward, et al., *Nature,* 341:544 (1989), all incorporated by reference herein.

For diagnostic purposes, the immunoglobulins may either be labeled or unlabeled. Unlabeled antibodies can be used in combination with other labeled antibodies (second antibodies) that are reactive with the first antibody, such as antibodies specific for human immunoglobulin constant regions. Alternatively, the antibodies can be directly labeled. A wide variety of labels may be employed, such as radionuclides, fluors, enzymes, enzyme substrates, enzyme co-factors, enzyme inhibitors, ligands (particularly haptens), etc. Numerous types of immunoassays are available and are well known to those skilled in the art.

For methods of the invention, particularly for therapeutic methods, the immunoglobulins can be coupled to another compound for a variety of reasons. For example, such a coupling may enhance transport, absorption, bioavailability and distribution of the immunoglobulin. For instance, the compound to which the immunoglobulin is coupled may make the immunoglobulin less susceptible to breakdown by normal enzymatic activity or it may make the immunoglobulin more transportable to certain physiologic compartments. For example, the immunoglobulin could be rendered more transportable across the blood brain barrier or perhaps more lipid soluble and thus more likely to be received into tissues with a high lipid content.

Also contemplated are those compounds that have designed specificities based upon the CDRs specific to a trk protein, such as those described here. Organic compounds may be synthesized with similar biological activity by first determining the relevant contact residues and conformation involved in trk binding by an antibody peptide of this invention. Computer programs to create models of proteins such as antibodies are generally available and well known to those skilled in the art (see Kabat, et al. *Sequences of Proteins of Immunological Interest,* U.S. Department of Health and Human Services, National Institutes of Health (1987); Loew, et al., *Int. J. Quant. Chem. Quant. Biol. Symp.,* 15:55–66 (1988); Bruccoleri, et al., *Nature* 335:564–568 (1988); Chothia, et al., *Science* 233:755–758 (1986), all of which are incorporated herein by reference. Commercially available computer programs can be used to display these models on a computer monitor, to calculate the distance between atoms, and to estimate the likelihood of different amino acids interacting (see, Ferrin, et al., *J. Mol. Graphics* 6:13–27 (1988)). For example computer models can predict charged amino acid residues that were accessible and relevant in binding and then conformationally restricted organic molecules can be synthesized. See, for example, Saragovi, et al., *Science* 253:792 (1991).

Other General Definitions

"Recombinant" means that the subject product is the result of the manipulation of genes by human intervention into new or non-native combinations.

"Restriction endonucleases" and "restriction enzymes" refer to enzymes which cut double stranded DNA at or near a specific nucleotide recognition sequence.

Complementary DNA, "cDNA" refers to DNA that is derived from a messenger RNA sequence (mRNA), for example, using reverse transcriptase. Reverse transcriptase is an enzyme that polymerizes DNA using an RNA template.

"Transcriptional activating sequences" refer to DNA sequences, such as promoters and enhancers, that activate transcription of a gene. Such sequences, in a proper host, drive transcription of a correctly positioned DNA sequence encoding a peptide. For example, the κ chain promoter and κ chain enhancer will promote transcription of a correctly positioned DNA sequence in a myeloma or hybridoma host. Other transcriptional regulator sequences will often be useful in analogous circumstances, for example, when deactivation may be desired.

"Coding strand sequence" is the region of a gene that encodes the amino acid sequence of a protein.

A "promoter" is a DNA sequence 5' of the protein coding sequences which affects transcriptional activity. RNA polymerase first binds to the promoter to initiate transcription of a gene.

An "enhancer" is a DNA sequence that can positively affect transcriptional efficiency. A preferred enhancer for the sequence encoding a heavy chain variable region of the antibodies described here is that found at base positions 1566 to 1813 on Sequence Listing ID No. 1.

A "vector" is a sequence of DNA, typically in plasmid or viral form, which is capable of replicating in a host. A vector can be used to transport or manipulate DNA sequences. An "expression vector" includes vectors which are capable of expressing DNA sequences contained therein, typically producing a protein product. The coding sequences are linked to other sequences capable of effecting their expression, such as promoters and enhancers. Expression vectors are capable of replicating in a host in episomal form; others can integrate into a host cell's chromosome. Ideally, the expression vectors have a selectable marker, for example, neomycin resistance, which permits the selection of cells containing the marker.

An "oligonucleotide" is a polymer molecule of two or more nucleotides including either deoxyribonucleotides or ribonucleotides.

"Host cells" refer to cells which are capable or have been transformed with a vector, typically an expression vector. A host cell can be prokaryotic or eukaryotic, including bacteria, insect, yeast and mammalian cells.

"Cellular material" or "cellular sample" refer to animal cells or portions thereof which can be, for example, whole cells, parts of cells (e.g., axon fragments or fragments of neurons) and lysates of cells or parts of cells.

Therapy

A patient having a neurologic condition suspected of being susceptible to treatment with a method of the invention is selected for therapy. Typically, the patient has a neurological condition discussed previously including the neurodegenerative disorders, nervous system cancer and epilepsy. Conditions including ischemia of any of the portions of the nervous system are included. For example, cerebral vascular ischemia and nerve tissue ischemia are appropriate conditions for therapy. The term "ischemia" refers to suboptimal oxygenation of tissue. The term "nerve tissue" refers to any portion of the nervous system of a recipient of a method of the invention. For instance, the central nervous system and peripheral nervous system are included in the term.

Using a therapeutic method of the invention, immunoglobulins are preferably administered to human patients parenterally. Preferably the compositions are administered in unit dosage forms suitable for single administration of precise dosage amounts. The compositions may also include, depending on the formulation desired, pharmaceutically-acceptable, non-toxic carriers or diluents, which are defined as vehicles commonly used to form pharmaceutical compositions for animal or human administration. The diluent is selected so as not to affect the biological activity of the combination. Examples of such diluents are distilled water, physiological saline, Ringer's solution, dextrose solution, and Hank's solution. In addition, the pharmaceutical composition or formulation may also include additives such as other carriers; adjuvants; or nontoxic, nontherapeutic, nonimmunogenic stabilizers and the like. Effective amounts of such diluent or additive are those amounts which are effective to obtain a pharmaceutically acceptable formulation in terms of solubility biological activity, etc.

In therapeutic applications, the dosage of immunoglobulins used in accordance with the invention will vary considerably depending on the condition being treated. The age, weight, and clinical condition of the recipient patient; and the experience and judgment of the clinician or practitioner administering the therapy are among the factors affecting the selected dosage. Typically, the dosage of immunoglobulin will range from about 1.0 microgram per kilogram per day to about 1 milligram per kg per day for polyclonal antibodies and about 5% to about 10% of that amount for monoclonal antibodies. For example, the immunoglobulin can be administered once daily as an intravenous infusion. Preferably, the dosage is repeated daily until either a therapeutic result is achieved or until side effects warrant discontinuation of therapy.

Generally, parenteral administration, such as intraventricular, intramuscular and intravenous administration, is preferred. Intraventricular administration refers to putting the immunoglobulin into any of the cavities of the nervous system including the left and right lateral ventricles, the third ventricle, the cerebral aqueduct, the fourth ventricle and the central canal. To put an immunoglobulin into any of these cavities usually involves placing a catheter into the cavity and pushing the immunoglobulin through the catheter and into the cavity. The catheter may be removed after a bolus infusion of the immunoglobulin or, preferably, a pump is implanted in the patient. The implanted pump pushes the immunoglobulin through the catheter and into the cavity in a predetermined and usually continuous fashion. Administration by an implanted pump technique can bypass certain problems of other methods of parenteral administration such as difficulties in physiologic transport across the blood brain barrier.

Therapeutic benefit includes any of a number of subjective or objective factors indicating a response of the condition being treated. For instance, some subjective symptoms of neurodegenerative disorders include pain, change in sensation including decreased sensation, muscle weakness, coordination problems, imbalance, neurasthenia, malaise, decreased reaction times, tremors, confusion, poor memory, and uncontrollable movement. Frequently objective signs, or signs observable by the physician or the health care provider, overlap with subjective signs. Examples include the physician's observation of signs such as decreased reaction time, muscle fasiculations, tremors, rigidity, spasticity, muscle weakness, poor coordination, poor memory, disorientation, dysphasia, dysarthria, and imbalance. Additionally, objective signs can include laboratory parameters such as the results of blood tests, biopsies and electrical studies such as electromyographic data. Additionally, nerve conduction studies can be performed to provide an objective criterion to evaluate the effect of therapy.

An example of an objective study which could show a therapeutic benefit in response to the methods of the invention is comparative biopsy. For instance, a nervous system cancer can be initially diagnosed and classified by a biopsy as is well known in the art. Subsequently, after a treatment using a method of the invention, a biopsy can be repeated. Parameters of the biopsy of the nerve cancer which could indicate improvement in response to the invention include an increased level of differentiation of the tumor as shown in the biopsy material. Additionally, growth markers or indicia of the speed of cell growth can be useful parameters to follow. For instance, a decrease in cell growth as noted by a decrease in thymidylate synthase activity has been correlated with decreased growth of certain tumors. Such a method could apply to the invention wherein a biopsy taken after a treatment with the invention is evaluated and which may show decrease in thymidylate synthase activity thus implying a decrease in tumor growth rate. Evaluation by biopsy applies to other neurologic conditions in addition to cancer. For instance, a biopsy can be useful in evaluating peripheral neuropathies and their response to treatment. The biopsy can be evaluated by a variety of methods known in the art such as histologic staining and analysis as well as by methods of the invention such as labeling with an immunoglobulin of the invention and applying histochemical techniques.

Also, macroscopic methods of evaluating the effects of the invention can be used, such as evaluating the tumor size or bulk clinically or by X-ray or other studies which may be invasive or noninvasive. Further examples of evidence of a therapeutic benefit include clinical evaluations for memory improvement, increased performance speed of defined tasks as compared to pretreatment performance speeds, and nerve conduction velocity studies. For example, it has been demonstrated that experimental animals deficient in NGF also suffer from poor memory retention. Evaluation of features such as memory, speed of performing defined tasks, and nerve conduction studies could also be used to indicate that appropriate trk receptors have been activated. Any of the features relating to therapeutic benefits can be examples of improved neuronal function.

TrkA, a tyrosine kinase receptor, is an essential component of the NGF response pathway. The binding of NGF to the receptor induces receptor autophosphorylation and activation of intracellular signaling pathways, resulting in diverse biological effects. Described herein is the preparation of antibodies against the entire extracellular domain of rat trkA produced using a baculovirus expression system. These antibodies specifically recognize rat trkA on antigen blots and in immunoprecipitations.

Both IgG and Fab fragments of the invention block binding of NGF to trkA expressed by the PC12 cell line. In NGF binding studies herein, anti-trkA and anti-low affinity NGF receptor (anti-LNGFR) IgG inhibited, essentially all binding of NGF. The results imply that at least 97% of the NGF binding sites on PC12 cells are accounted for by trkA and the LNGFR. The binding data also argue that all low affinity NGF binding sites on PC12 cells reflect interactions with the LNGFR, while all high affinity sites are trkA-dependent. A fraction of the high affinity sites seem to require both trkA and the LNGFR.

While the monovalent anti-trkA Fab fragments of the invention inhibited the biological effects of NGF, such as induction of tyrosine phosphorylation and survival and neurite outgrowth of sympathetic neurons, the IgG preparation surprisingly was not effective as an inhibitor. Instead, the IgG fraction by itself was almost as effective as NGF at stimulating receptor activation and cell survival. Thus, it appears that oligomerization of trkA by antibody-induced crosslinking produces cellular effects of NGF.

Development of an Antiserum to the Rat trkA Receptor

Generation of antisera to both the LNGFR and trkA receptors allows the expression and function of each to be studied individually. Several monoclonal antibodies and the REX anti-LNGFR polyclonal antibody have been used to characterize the LNGFR receptor, but an antiserum of equivalent specificity to trkA has not been available previously. The invention is illustrated by a bivalent IgG antibody, RtrkA.EX, which is highly specific for trkA. No cross-reaction with the closely related trkB receptor on immunoblots was detected.

A discrete immunohistochemical staining pattern in mouse brain consistent with what is known about trkA gene expression has seen. The RtrkA.EX antibody recognizes the rat trkA receptor in its native state, as judged by immunoprecipitation analysis, and is therefore useful in a variety of experiments aimed at improved understanding of trkA and NGF responsiveness in neurons. The anti-trkA IgG promoted NGF-like cellular responses even in the absence of NGF, presumably through antibody-dependent receptor cross-linking.

Figure 3:
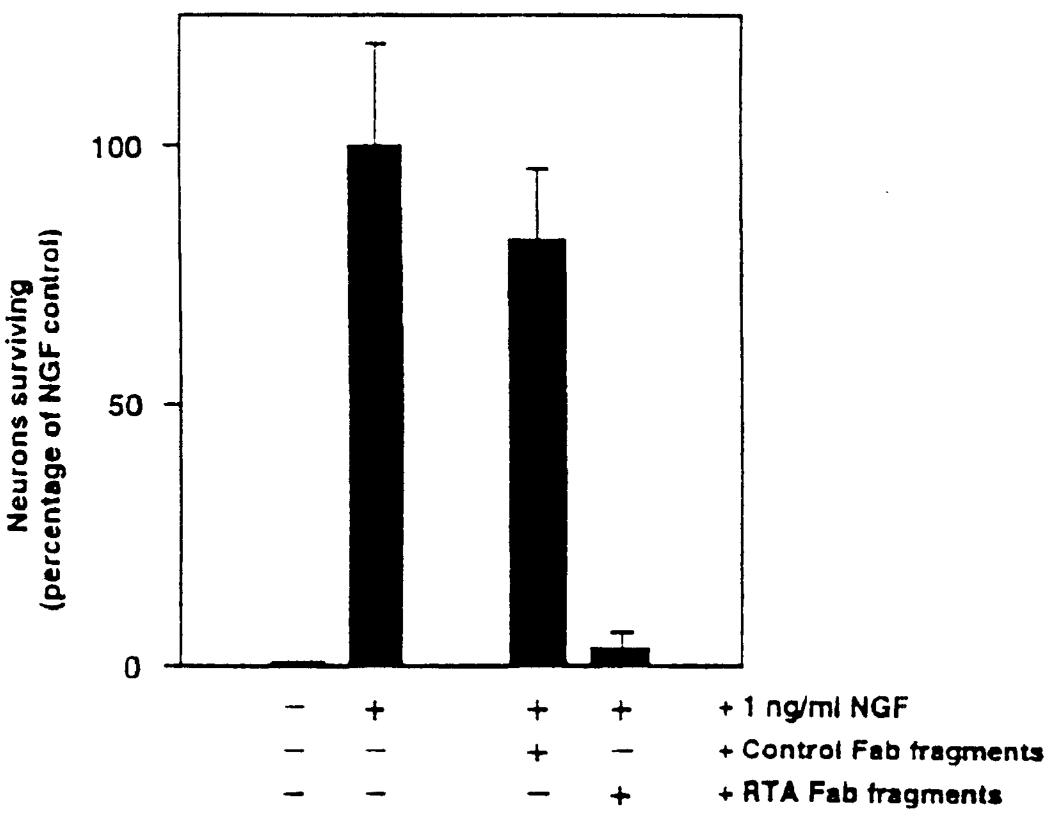
FIG. 3 is a graph of neuron survival after treatment with antibody fragments of the invention.

An antibody of the invention can inhibit NGF binding, as well as neuronal responses to NGF, when Fab fragments were employed. NGF binding experiments demonstrated that monovalent Fab fragments prepared from the RtrkA.EX antibody inhibit NGF binding to trkA (FIG. 1), and subsequently inhibit downstream cellular NGF responses, such as increases in tyrosine phosphorylation and survival of sympathetic neurons (FIG. 3).

The use of monovalent Fab fragments for trkA receptor blocking can be a useful method for confirming or disproving in an in vivo context some of the functions assigned to NGF based on in vitro studies. In fact, this could be a general approach to studying the roles of trk receptors during development in many species. Since it is thought that several of the functions of trk receptors are based on competition for limiting amounts of neurotrophin in the animal (Barde, 1989), blocking a large number of the receptors by Fab could yield dramatic effects during development. Data herein indicates blockage of sympathetic survival only at low concentrations of NGF and high concentrations of Fab, which is likely due to the differences in receptor affinity. However, given that in vivo concentrations of NGF are much lower than those used in culture, it is possible that this Fab preparation would be an effective means of blocking trkA function in developing rats or mice.

An "Fab" fragment comprises a light chain and the N-terminus portion of the heavy chain to which it is linked by disulfide bonds. It has a molecular weight of approximately 50 kD and contains a single antigen binding site. Fab fragments may be obtained from $F(ab')_2$ fragments by limited reduction, or from whole antibody by digestion with papain in the presence of reducing agents (see Harlow and Lane, supra).

Ligand-independent Activation of trkA by RtrkA.EX

While the IgG and Fab preparations of the RtrkA.EX sera are equivalent in their ability to inhibit NGF binding to trkA, as judged by binding assays using radiolabeled ligand, the RtrkA.EX IgG is almost as effective as NGF in activating trkA and downstream signaling pathways.

Evidence has been presented that the trkA receptor functions as a homooligomer, probably a dimer, in signal transduction (Jing, et al., 1992). Therefore, it is likely that the bivalent RtrkA.EX IgG promotes dimerization or oligomerization sufficient to cause transphosphorylation of the receptor and subsequent activation of the NGF signal transduction pathway.

The RtrkA.EX antibody at saturating concentrations exhibits a somewhat lower survival activity than NGF. This seems to be an intrinsic property of the receptor-antibody interaction. Because the presence of NGF does not restore the maximal level of survival, the lack of NGF bound to the LNGFR is not likely the cause.

Activation of trkA by RtrkA.EX is a useful method for separating the effects of trkA from those of the LNGFR. In fact, this property can be exploited to differentiate the effects of the three receptors of the trk family, as antibodies have the potential to be of different specificity from the neurotrophins themselves.

For example, in some systems NT-3 has been shown to activate trkC strongly, to activate trkB moderately, and to activate trkA weakly (Cordon-Cardo, et al., *Cell.* 66:173–83 (1991); *Glass*, et al., *Cell.* 66:405–13 (1991); Squinto, et al., *Cell.* 65:885–93 (1991); Soppet, et al., *Cell.* 65:895–903 (1991); Lamballe, et al., (1991)). Studies designed to analyze the various functions of trkC by using NT-3 as ligand may also be measuring its effects on trkb or trkA. An activating antibody to trkC, however, would produce effects which are attributable solely to trkC.

TrkA Activity, but not LNGFR Activity, is Required for Sympathetic Neuron Survival in Vitro The experiments herein evaluate the relative contributions of LNGFR and trkA in high affinity NGF binding and in the NGF-dependent survival of sympathetic neurons. One of the models of LNGFR function holds that LNGFR and trkA form a high-affinity heterodimer, and that the LNGFR participates in the NGF signal transduction pathway (Hempstead, et al., 1991; Berg, et al., 1991). It now seems clear that activation of trkA is necessary and sufficient to achieve most cellular NGF effects, at least under in vitro culture conditions. This is born out by the finding herein that in the absence of NGF the RtrkA.EX IgG facilitates survival and differentiation of both sympathetic neurons and PC12 cells by activating trkA. Several previous observations also support this conclusion. Evidence that trkA is a necessary component of the NGF responsive pathway in PC12 cells comes from studies of the trkA-deficient cell line PC12nnr5, where it was shown that its lack of NGF response could be rectified by the reintroduction of trkA (Loeb, et al., *Cell.* 66:961–6 (1991)).

There are several lines of evidence which suggest that the LNGFR does not play a crucial role in NGF signal transduction. The anti-LNGFR polyclonal antibody REX was able to block binding of NGF to LNGFR completely, yet had no obvious effect on the biological activities of NGF in culture (Weskamp and Reichardt, 1991). In agreement with this result, a mutated NGF which had lost its ability to bind to LNGFR was able nevertheless to support neurite outgrowth from PC12 cells and survival of neonatal sympathetic neurons (Ibáñez, et al., *Cell.* 69:329–41 (1992)). A recent study, published after the completion of the present work, examined the activity in PC12 cells of a chimeric receptor consisting of the trkA intracellular kinase domain fused to the tumor necrosis factor receptor extracellular domain, and found that treatment of the modified PC12 line with tumor necrosis factor could promote PC12 process outgrowth, presumably without interaction with the LNGFR (Rovelli, et al., *Proc. Natl. Acad. Sci. USA* 90:8717–8721 (1993)).

In each of the above examples, it is assumed that the LNGFR is not contributing to the NGF response if the LNGFR is not binding ligand, something which is difficult to prove using those models. Jaenisch and colleagues have addressed this issue by creating a mouse strain in which the gene for the LNGFR has been inactivated (Lee, et al., *Cell.* 69:737–49 (1992)). The resulting mice were viable and fertile. Examination of the nervous system revealed a loss of some sensory innervation and a defect in heat sensitivity, although the sympathetic innervation was apparently normal. Examination of the in vitro sensitivity to NGF of the trigeminal sensory neurons and sympathetic neurons has recently been reported; while a three- to four-fold decrease in the NGF dose-response was measured for the sensory neurons, no differences were detected between the LNGFR-deficient and wild type sympathetic neurons (Davies, et al., *Neuron.* 11:565–574 (1993)). Thus for at least some of the targets of NGF, the LNGFR is not required either in an NGF-bound or unbound state for NGF to achieve its effects.

An interesting model proposed recently has the LNGFR acting in a dominant fashion: when the receptor is bound by ligand, it is inactive, but when unbound it is free to activate-a cellular pathway leading to apoptotic cell death (Rabizadeh, et al., 1993). Evidence herein argues against this model for sympathetic neurons, as activation of trkA by RtrkA.EX in the absence of NGF (and therefore when the LNGFR is presumably unbound) could support sympathetic neuron survival, and the combination of RtrkA.EX and NGF did not yield much more survival than the antibody alone. At a minimum, the activation of the trkA signaling pathway overrides the putative LNGFR-dependent apoptotic pathway. As the model suggests that the LNGFR works in a dominant fashion to cause apoptosis, it does not easily explain the deficits observed in the LNGFR-deficient mouse. If the dominant model of LNGFR action is correct, the deletion of the LNGFR gene might actually be expected to increase the number of cells in certain populations, rather then eliminate them, and would be unlikely to lead to the observed deficit in sensory innervation.

The foregoing is offered primarily for purposes of illustration. It will be readily apparent to those skilled in the art that the operating conditions, materials, procedural steps and other parameters of the system described herein may be further modified or substituted in various ways without departing from the spirit and scope of the invention. Thus the invention is not limited by the preceding description and the following examples, but rather by the appended claims.

EXAMPLES

Example 1

Preparation of an Antibody Against the Extracellular Domain of Rat trkA

To probe the function of the trkA receptor biochemically and biologically, a polyclonal antibody was developed to the extracellular domain of trkA.

Rabbit polyclonal antisera recognizing rat trkA were generated by using as antigen synthetic peptides derived from the rat trkA amino acid sequence coupled to keyhole limpet hemagglutinin by m-maleimidobenzoylsulfosuccinimide ester (Pierce Chemical Co.). One of the antisera (rtrkA.EX2) was raised against the peptide CSVLNETSFIFTQFLESALTNETMRH (amino terminal cysteine+trkA amino acids 322 to 346) and recognized the extracellular domain of trkA by immunoblot.

Another antibody (rtrkA.cyt) was raised against a peptide corresponding to the carboxy-terminal end of the rat trkA receptor (CARLQALAQAPPSYLDVLG; amino terminal cysteine+trkA amino acids 782 to 799) and was subsequently affinity purified on a column including the same peptide coupled to thiopropyl-Sepharose CL-6B (Pharmacia LKB Biotechnology).

Generation of a third trkA antiserum, denoted RtrkA.EX antibody and abbreviated RTA or RtrkA.Ex, is outlined below. Briefly, cDNAs encoding rat trkA were isolated from a PC12 cDNA library constructed in the plasmid vector CDM8. Ten cDNAs were isolated, and sequence analysis revealed that several of these contained the entire rat trkA coding sequence.

cDNA Cloning

A PC12 cDNA library was constructed in the plasmid vector CDM8 using nonpalindromic adaptors (Invitrogen Corp., San Diego, Calif.) essentially as described (Seed, B., *Nature,* 329, 840–842 (1987); Aruffo, A. and Seed, B., *Proc. Natl. Acad. Sci. USA,* 84, 8573–8577 (1987)). A probe for the rat trkA cDNA was generated from cDNA derived from the human cell line K562 (Martin-Zanca, et al., 1989) using reverse transcription—polymerase chain reaction (RT-PCR) and the primers 5' GGC CGA ATT CGC CCG GCG CAG AGA ACC TGA CTG AGC (SEQ ID NO:3) and 5' GGC CGA ATT CAT GTG CTG TTA GTG TCA GGG ATG GGG, (SEQ ID NO:4) which yields a 1027 base pair (bp) fragment (coding for amino acids 63 to 397) derived from the region of the transcript encoding the extracellular domain.

Bacterial colonies harboring rat trkA-containing plasmids were isolated using colony hybridization (Sambrook, et al., *Molecular Cloning: A Laboratory Manual,* 2d ed. (1989)). cDNA inserts were recloned into Bluescript vectors and sequenced using the dideoxynucleotide-termination method (Sequenase; United States Biochemical Co.). The sequence obtained agreed with that published previously (Meakin, S. O., Suter, U., Drinkwater, C. C., Welcher, A. A. and Shooter, E. M., *Proc. Natl. Acad. Sci. USA,* 89, 2374–8 (1992)), with the exception of a slightly shorter 5' untranslated region.

A truncated trkA expression cassette containing the entire extracellular domain of rat trkA was generated by polymerase chain reaction (PCR) and its DNA sequence verified. The cassette was subsequently cloned into a baculovirus transfer vector from which recombinant viruses were isolated though standard protocols.

Construction of a Baculovirus Strain Expressing a Rat trkA Truncation

PCR was used to generate a version of the rat trkA cDNA which could direct expression of a truncated form of the receptor. The primers used were:

5' CCG AAT TCC ATG GCG CGA GGC CAG CGG CAC GGG CAG CTG G 3' (SEQ ID NO:5) (5' end of cassette) and 5' CCG AAT TCC ATG GCT ATT ATT CGT CCT TCT TCT CCA CTG GGT CTC (SEQ ID NO. 6 3' (3' end of cassette).

The resulting DNA construct was flanked by EcoRI and NcoI restriction sites, and contained the DNA sequence between the presumptive start methionine codon and the glutamic acid codon before the transmembrane domain (therefore encoding amino acids 1 to 416; called RtrkA.t).

The construct was cloned into the baculovirus transfer vector pVL1393 (Webb, N. R. and Summers, M. D., *Technique.,* 2, 173–188 (1990)) using EcoRI sites. The resulting plasmid was used to transfer the RtrkA.t construct into a linearized baculovirus ACMNPV genome (Invitrogen Corp.), and purified recombinant viruses which express the truncated form of the trkA receptor were isolated using standard methods (Summers and Smith, *A Manual of Methods for Baculovirus Vectors and Insect Cell Culture Procedures,* Texas Agricultural Experimental Institute (1987); Webb and Summers, 1990). Recombinant viruses were identified using PCR and oligonucleotide primers specific for RtrkA.t construct and the AcMNPV genome (Invitrogen Corp.)

Infections of Sf9 cells (ATCC No. CRL 1711) with the recombinant virus resulted in the production of an approximately 55 kilodalton (kD) product which was secreted into the medium. The expression of the truncated trkA protein was monitored by immunoblotting with an anti-trkA peptide antiserum, and the protein was purified.

Purification of RtrkA.EX Protein and Generation of the RtrkA.EX Antibody

Large scale infections with the RtrkA.EX-expressing baculovirus were performed using the Sf9 cell line (the gift of W. Mobley) grown in Sf9 II SFM medium (Gibco/BRL, Life Technologies). The levels of RtrkA.EX protein throughout expression and purification procedures were measured by antigen blot with the rtrkA.EX2 anti-peptide antibody.

For purification, 1.2 liters (l) of Sf9 cells were infected with 160 milliliters (ml) of high titer viral stock, and two days post-infection, the supernatant was harvested and loaded onto a 10 ml lentil lectin-Sepharose column (Pharmacia/LKB Biotechnology).

After washing with 500 mM NaCl and 5 mM Tris-Cl at pH 7.5, protein was eluted with 5 mM Tris-Cl, pH 7.5, 150 mM NaCl, 0.5 M methyl-a-D-mannopyranoside (Sigma Chemical Corp.). The eluate was dialyzed into 20 mM Tris-Cl pH 8.0, concentrated by pressure on a YM30 membrane (Amicon), and loaded onto a MonoQ column (1 ml; Pharmacia/LKB Biotechnologies).

After washing the column with 20 mM Tris-Cl at pH 8.0, the column was developed with a linear gradient to 20 mM Tris-Cl, pH 8.0, 1 M NaCl. The RtrkA.EX protein eluted in a peak at approximately 200 mM NaCl, and ran on sodium dodecyl sulfate-polyacrylamide gel electrophoresis (SDS-PAGE) as an overlapping doublet of approximately 55 kD molecular weight, with a typical yield of 500 $\mu$g.

Both of the doublet bands reacted strongly with the rtrkA.EX2 antibody, indicating that each was derived from the trkA expression vector but differed by post-translational modification such as glycosylation. The identity of the purified-protein was confirmed by the amino acid sequence analysis of two peptides derived from a trypsin digestion of the preparation.

The protein's identity was confirmed by determining the amino acid sequences of two tryptic peptides derived from it. The truncated trkA protein was subsequently used as an immunogen to raise rabbit polyclonal antisera. This antibody is referred to herein as the RtrkA.EX antibody (abbreviated as RTA).

The purified protein was used to immunize a rabbit with an initial injection of 175 micrograms (μg) of protein; subsequent boosts were 50 μg each. IgG was prepared from the resulting sera by affinity chromatography on protein-A Sepharose by standard methods (Harlow and Lane, *Antibodies: A Laboratory Manual,* Cold Spring Harbor Laboratory Press, New York (1988)).

Immunoblots and immunoprecipitations.

The ability of the RtrkA.EX sera to recognize native rat trkA was tested by immunoprecipitation analysis, using lysates of COS cells surface-labeled with biotin following transfection with CDM8/rat trkA, or with vector alone as control.

Lysis buffer contained: 150 mM NaCl; 50 mM Tris-Cl, pH 7.6; 1% Triton X-100; 0.1% sodium dodecyl sulfate; 1 mM ethylenediaminetetraacetic acid; 1 mM phenylmethylsulfonyl fluoride; 50 mM NaF; and 10 mM sodium pyrophosphate. When the lysates were to be probed for phosphotyrosine, the lysis buffer contained 0.1 mM sodium orthovanadate in addition.

Extracts were prepared by incubating cells with lysis buffer on ice for 15 minutes; insoluble material was removed with a 10,000 rpm centrifugation at 4° C. for ten minutes. Extracts were separated on SDS-polyacrylamide gels and transferred to nitrocellulose using standard protocols (Harlow and Lane, 1988).

TrkA immunoprecipitations were performed by adding 2–10 μg of IgG and 30 ml of protein A-Sepharose per sample. After two to three hours at 4° C., the Sepharose was washed four times with lysis buffer. Sepharose-bound proteins were eluted in two times volume of Laemmli SDS sample buffer and loaded on SDS-PAGE for immunoblot analysis.

For biotinylation, COS cell cultures which had been transfected with cDNA constructs two days previously were washed two times with calcium- and magnesium-free phosphate buffered saline (CMF-PBS). CMF-PBS+100 mM Hepes at pH 8.0 and 360 μg/ml sulfosuccinimidobiotin (Pierce Chemical Corp.) was added and the cultures were incubated for one hour at room temperature. The cultures were washed four times with phosphate buffered saline (PBS)+5 mM glycine and lysates were prepared as above. The extracts were precleared with protein-A sepharose, and immunoprecipitations were performed as described above.

After immunoprecipitations were performed with either RtrkA.EX, an anti-peptide antibody to the trkA cytoplasmic tail (rtrkA.cyt), or control IgGs, the precipitates were analyzed by blot using a streptavidin-horseradish peroxidase (HRP) conjugate for detection (FIG. 1A). The HRP-coupled streptavidin was purchased from Zymed Laboratories, Inc.

Immunoblots were performed using 80 mM NaCl, 50 mM Tris-Cl at pH 8.0, 0.5% Nonidet P-40 and either 5% nonfat milk or 3% bovine serum albumin. 1% ovalbumin was used when HRP-coupled secondary antibodies were used.

The anti-phosphotyrosine monoclonal antibody 4G10, purchased from Upstate Biologicals Inc., was used at 1 μg/ml, followed by rabbit anti-mouse antibody, purchased from Organon Teknika Corp., coupled to HRP diluted 1:5000.

Streptavidin-HRP was also used at 1:5000 dilution; the alkaline phosphatase coupled secondary antibody (alkaline phosphatase-conjugated goat anti-rabbit antibody obtained from Promega Corp.) was used at 0.1 μg/ml and was developed using the BCIP/NBT method (Harlow and Lane, 1988). HRP conjugates were detected with the ECL chemiluminescence protocol (supplied by the manufacturer with the reagent) developed by Amersham Corp.

COS cell cultures were transfected with CDM8 vector alone (V) or with CDM8 containing the rat trkA cDNA (T) and were subsequently cell surface-labeled with sulfosuccinimidobiotin. The resulting extracts were used for immunoprecipitation as follows: 100 μg of extract (CDM8 extract, lane 1; CDM8/trkA extract, lanes 2–5) were precipitated with the addition RtrkA.EX IgG (lanes 1 and 5), rat trkA cyto-tail IgG (lane 4), nonimmune rabbit IgG obtained from organon Teknika Corp. (lane 3), or no antibody (lane 2).

After precipitation with protein-A Sepharose, the immune complexes were separated on 7.5% SDS polyacrylamide gels, transferred to nitrocellulose, and visualized with peroxidase-coupled streptavidin and the ECL chemiluminescence protocol (Amersham Corp.).

RtrkA.EX was able to precipitate the 140 kD trkA protein efficiently (lane 5), as shown by comparison to the same lysate precipitated with an antibody directed against the cytoplasmic tail of trkA (lane 4). A set of weak bands with an approximate mass of about 110 kD in both lanes were likely immature forms of the trkA receptor which have been transported to the cell surface (Martin-Zanca, et al., 1989) or derived from the 140 kD form of trkA by proteolysis. The trkA products were not detected in control lysates derived from a vector-only transfection precipitated with RtrkA.EX (lane 1), or in precipitates of trkA-transfected cells using control rabbit IgG (lane 3). Several proteins of lower apparent molecular weight were detected in each of the precipitates, including controls, and therefore appear to be nonspecific contaminants.

The specificity of the RtrkA.EX antibody was also tested by immunoblot using the method described above. Immunoblotting of cell extracts from COS cell cultures was done as follows. The antigen blot was derived from a 7.5% PAGE of COS cell lysates (7 μg each) transfected with the CDM8 vector (lane 1), CDM8/rat trkA (lane 2), or CDMS/rat trkB (lane 3). The filter was incubated with 0.5 mg/ml RtrkA.EX IgG, followed by an anti-rabbit-alkaline phosphatase secondary antibody. The expression of the trkB in lane 3 was confirmed by blotting a parallel experiment with an anti-trkB cytoplasmic tail antibody. COS cell cultures were transfected as above with the rat trkA or rat trkB cDNAs, or vector alone, and lysates from all three cultures were probed with the RtrkA.EX sera.

Two prominent bands were detected in the lysate of the trkA transfected culture, migrating at an approximate molecular mass of 110 kD and 140 kD. No cross-reaction to trkB was detected, although it was abundantly expressed, as determined by probing a parallel blot with an antibody against the trkB cytoplasmic tail. A faint band was detected in all three lysates, migrating with an approximate molecular mass of 180 kD. This band seemed to be a nonspecific reaction of the sera, as it was seen in untransfected COS cells, as well as other cell lines (including the PC12 cell line). It was not detected by immunoprecipitation, indicating that either it was an intracellular protein and therefore not labeled by the biotinylation reagent, or that it was not recognized by the antibody in an undenatured state.

Example 2

RtrkA.EX Blocks the Binding of NGF to the trkA Receptor

From the immunoprecipitation analysis it was clear that the RtrkA.EX antibody can recognize the native trkA receptor protein. To determine if the antibody could disrupt the NGF-binding activity of the receptor, and therefore serve as an inhibitor of the receptor's function, the following experiments were done. In this series of experiments, the effects of the antibody preparations were tested in NGF binding assays of the PC12 cell line, known to express both the low affinity NGF receptor LNGFR as well as trkA. NGF was purified from male mouse submaxillary gland following the procedure of (Mobley, W. C., Schenker, A. and Shooter, E. M., *Biochemistry.,* 15, 5543–5552 (1976)) or was the gift of W. Mobley.

Cell Culture

PC12 cells (ATCC No. CRL 1721) were maintained in Dulbecco's Modified Eagle's medium (DME-H21) containing 10% fetal calf serum and 5% horse serum on tissue culture plastic. The nnr5 subclone of PC12 (available from Dr. Lloyd Greene, New York University School of Medicine, NYC, N.Y. 10016) and its transfected derivatives were grown in the same medium on a collagen I substrate (Vitrogen 100, Celtrix Pharmaceutical, Inc.). PC12 cells used for outgrowth experiments were treated with NGF in DME-H21 containing 1% horse serum for seven days prior to replating in the same medium supplemented with NGF or antibodies.

A whole cell binding assay containing 200 pM $^{125}$I-NGF was employed to measure the dose-dependent inhibition of binding (FIG. 1A). $^{125}$I-NGF was purchased from Amersham Corp.

FIG. 1 shows data indicating that RtrkA.EX IgG and Fab fragments block NGF binding to PC12 cells. FIG. 1A shows a dose response. PC12 cells were incubated with antibodies at the indicated concentration for four hours at 37° C., and binding was initiated by the addition of 200 pM $^{125}$I-NGF. After a one hour incubation, the amount of cell-associated NGF was determined. Antibodies tested were control rabbit IgG, RtrkA.EX IgG, and RtrkA.EX Fab fragments. Fab fragments were prepared from nonimmune rabbit IgG or the RtrkA.EX IgG using papain-agarose (Sigma Chemical Co.) by standard methods (Harlow and Lane, 1988). Nonspecific binding was determined by addition of 10 $\mu$g/ml unlabeled NGF, and has been subtracted. Values were determined in triplicate and are shown as percent control (no antibody addition).

The RtrkA.EX IgG and Fab preparations were able to inhibit the binding of NGF to PC12 cells partially, achieving a maximum inhibition of about 30%. Approximately 125 mg/ml antibody was required to reach this maximal level of inhibition.

Binding Assays

Binding assays were performed with PC12 cells and $^{125}$I-NGF as previously described (Weskamp and Reichardt, 1991). Briefly, antibodies were preincubated with the cells ($5\times10^5$ cells/ml) at 37° C. for two or four hours prior to addition of $^{125}$I-NGF; cell-associated NGF was determined after a further 60 minutes at 37° C. Nonspecific binding was determined by addition of 10 mg/ml unlabeled NGF, and ranged from 2–25% of specific binding. Determinations were made in triplicate. The equilibrium binding data from two experiments were combined for the Scatchard analysis (Scatchard, G., *Analys of NY Acad. Sciences* 5:660–672 (1949)), which was performed with the program LIGAND (Munson, P. J. and Rodbard, D., *Anal. Biochem.,* 107, 220–239 (1980)). The Scatchard data are plotted as fmoles bound per $10^5$ cells (equivalent to a volume of $2\times10^{-4}$ liters).

Figure 1B:
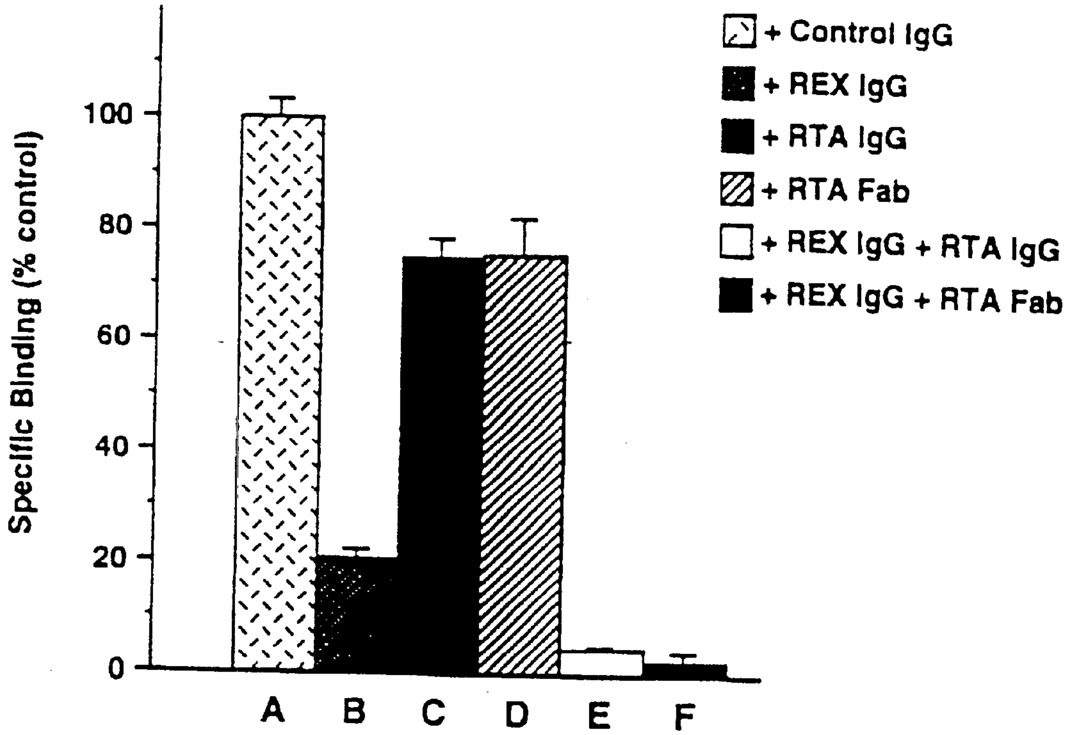
FIG. 1B is a whole-cell binding bar graph showing the additive effects of an antibody of the invention and another antibody.

Furthermore, the data show that the residual NGF binding in the presence of RtrkA.EX was due to binding to the low affinity NGF receptor, by testing saturating concentrations of antibodies to both trkA and the LNGFR (FIG. 1B). Here, NGF binding assays on PC12 cells were performed in the presence of RtrkA.EX IgG or Fab, anti-rat LNGFR IgG, or combinations of the antibodies, using the method described above.

The anti-LNGFR antibody (anti-REX; Weskamp and Reichardt, 1991) is an anti-rat polyclonal antiserum raised against the extracellular domain of LNGFR, and has been shown to inhibit NGF binding to that receptor completely.

FIG. 1B shows the additive effects of RtrkA.EX and anti-LNGFR antibodies. PC12 cells were incubated at 37° C. for four hours with 500 $\mu$g/ml of each indicated antibody, followed by the addition of 250 picomolar (pM) $^{125}$I-NGF. After a further 60 minutes at 37° C., the amount of cell-bound NGF was determined. Antibodies tested were: A, control rabbit IgG; B, anti-LNGFR IgG (REX); C, RtrkA.EX IgG (RTA); D, RtrkA.EX Fab fragments; E, anti-LNGFR IgG+RtrkA.EX IgG; and F, anti-LNGFR IgG+RtrkA.EX Fab fragments. Nonspecific binding was determined as in FIG. 1A; values are shown as a percentage of the control (no antibody addition). The values shown are the average of two experiments of triplicate samples and include calculated standard error of the mean.

As shown in FIG. 1B, the anti-LNGFR antibody blocked approximately 80% of NGF binding, while the RtrkA.EX IgG or Fab blocked approximately 25% of NGF binding. The combinations of antibodies were able to inhibit almost completely the binding of NGF to PC12 cells, indicating that trkA and the LNGFR account for at least 97% of the NGF binding proteins on PC12 cells.

Confirmation of the RtrkA.EX specificity was obtained using NGF cross-linking assays (Weskamp and Reichardt, 1991), where preincubation of the cells with the RtrkA.EX antibody sharply reduced the production of the 160 kD band, previously identified as the trkA $^{125}$I-NGF cross-linked product, without altering the levels of the 100 kD, LNGFR-derived product (Hosang and Shooter, 1985; Johnson, et al., 1986; Weskamp and Reichardt, 1991; Kaplan, et al., 1991a; Klein, et al., 1991).

To analyze the characteristics of the NGF binding sites remaining in the presence of the anti-LNGFR or -trkA antibodies, equilibrium binding assays were performed from 3.5 to 4000 pM NGF. The results are plotted by the Scatchard method in FIG. 2. As is now well known, PC12 cells have NGF binding sites with differing kinetic characteristics, leading to low and high affinity binding sites (Schechter and Bothwell, 1981). This is observed in the biphasic graph of NGF binding determined in the presence of control IgG (FIG. 2, open squares; the binding parameters are presented in Table 1).

TABLE 1*

Effects of anti-LNGFR and RTrkA.EX IgG on Equilibrium Binding of $^{125}$I-NGF to PC12 Cells

| Control IgG | | anti-LNGFR IgG | | RTrkA.EX IgG | |
|---|---|---|---|---|---|
| $K_d$ (M) | Receptors per Cell | $K_d$ (M) | Receptors per Cell | $K_d$ (M) | Receptors per Cell |
| 3.8 (±1.9) × $10^{-11}$ | 4900 ± 700 | 9.2 (±2.6) × $10^{-11}$ | 2800 ± 400 | — | — |
| 1.8 (±0.7) × $10^{-9}$ | 3400 ± 3200 | — | — | 1.1 (±0.6) × $10^{-9}$ | 28300 ± 3000 |

Figure 2:
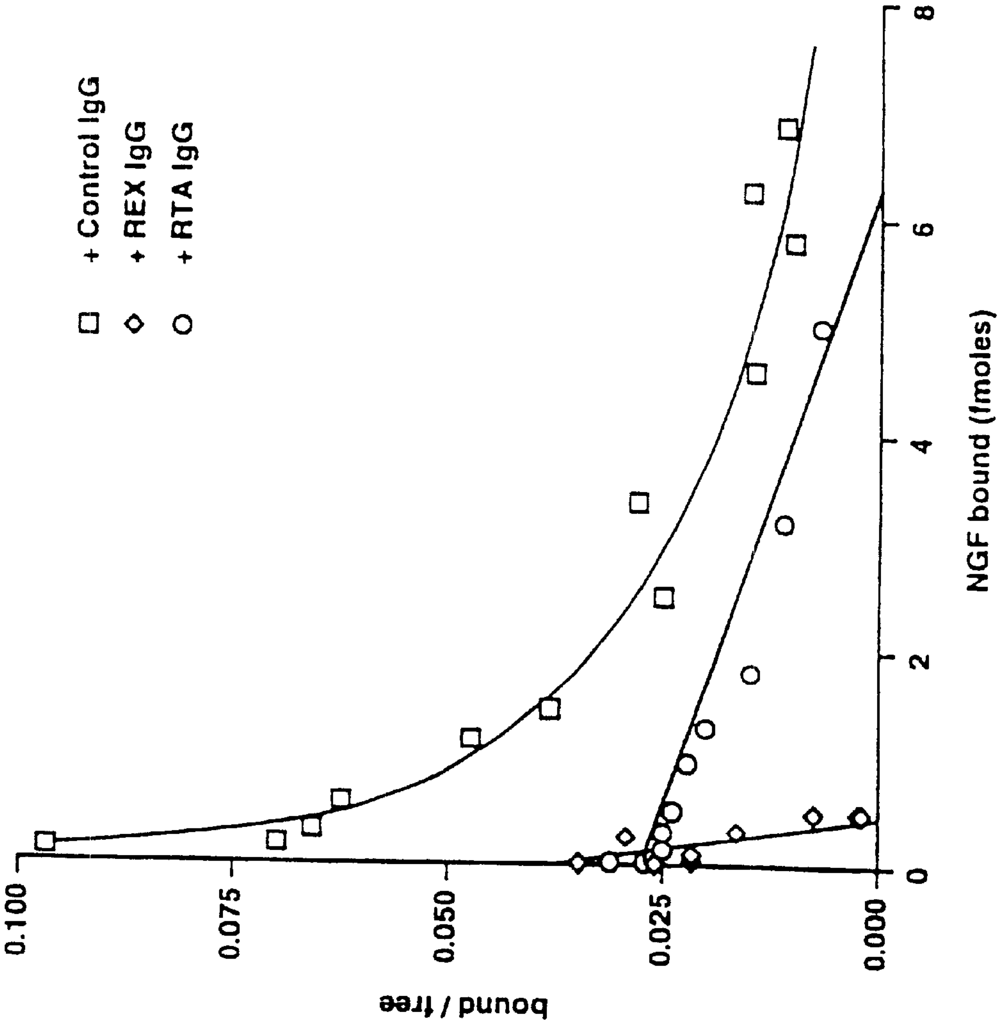
FIG. 2 is an analysis of NGF binding cites resistant to two antibodies of the invention.

*Binding parameters derived from the Scatchard analysis shown in FIG. 2, as determined by the LIGAND program.

FIG. 2 is an analysis of anti-LNGFR- and RtrkA.EX-resistant NGF binding sites. PC12 cells were preincubated with 500 μg/ml control rabbit IgG, anti-LNGFR (REX) IgG, or RtrkA.EX (RTA) IgG for two hours at 37° C. $^{125}$I-NGF (3.5 pM to 4 nM) was added, and the amount of cell associated NGF determined after one hour at 37° C. Data from two similar experiments were pooled, and are presented in the form of a Scatchard plot. Nonspecific binding was determined as in FIG. 1A; values were determined in triplicate.

The number and affinity of the two measured NGF binding sites in the presence of control IgG are similar to those previously reported for PC12 cells (Weskamp and Reichardt, 1991). Preincubation with anti-LNGFR IgG blocks all of the low affinity sites, and blocks a fraction of the high affinity sites, as shown previously (FIG. 2, diamonds; Weskamp and Reichardt, 1991). In contrast, the data herein show that in the presence of the RtrkA.EX antibody, all of the remaining detectable binding sites are of low affinity (FIG. 2, open circles). These results indicate that all detected high affinity binding sites require trkA. However, this analysis also suggests that there may be two types of high affinity sites, one which is dependent solely on trkA, and one of which requires both trkA and the LNGFR. No evidence was found for high affinity sites solely dependent on the LNGFR.

Example 3

RtrkA.EX Fab Fragments Inhibit the Phosphorylation Response to NGF

PC12 cells respond to NGF rapidly, and after five minutes of exposure, a reproducible burst of tyrosine phosphorylation of many cellular proteins occurs (Maher, P. A., *Proc. Natl. Acad. Sci. USA* 85:6788–6791 (1988)). This effect can be measured by probing blots of cell lysates with anti-phosphotyrosine antibodies. In lane 2 several cellular substrates for NGF-dependent tyrosine phosphorylation are detected after five minutes of NGF treatment (arrows), but not in the absence of NGF (lane 1).

RtrkA.EX Fab fragments block NGF-dependent cellular tyrosine phosphorylation. PC12 cultures were preincubated with 500 μg/ml nonimmune Fab (control, lane 3), RtrkA.EX Fab (RTA, lane 4), or no antibody (lanes 1 and 2), for four hours prior to the addition of 5 ng/ml NGF for five minutes (lanes 2–4). The cleared lysates (10 μg) were fractionated by 10% SDS-PAGE, blotted, and probed for changes in cellular tyrosine phosphorylation using the 4G10 monoclonal, HRP-coupled anti-mouse secondary antibody, and ECL. The positions and relative molecular weights of the marker proteins are shown at the left, and the arrows on the right indicate several prominent proteins which become hyperphosphorylated during the assay.

The ability of the anti-trkA antibody to block this rapid response was tested by pretreating the PC12 cultures with RtrkA.EX Fab fragments, or control nonimmune Fab fragments prior to exposure to NGF. RtrkA.EX Fab fragments were able to block almost completely the phosphorylation response to NGF (lane 4), while control nonimmune Fab fragments did not affect the response (lane 3).

Example 4

RtrkA.EX IgG Mimics NGF in Tyrosine Phosphorylation Assays

In contrast to the inhibitory effects of the monovalent RtrkA.EX Fab fragments, the bivalent RtrkA.EX IgG promoted phosphorylation of the same cellular proteins as NGF, even in the absence of NGF.

RtrkA.EX IgG stimulates protein tyrosine phosphorylation in the absence of ligand. PC12 cells were treated for five minutes with growth factors or antibody preparations at 37° C. Lysates were prepared and analyzed for changes in cellular phosphotyrosine as described in Example 3. The treatments were: no addition (lane 1); 50 ng/ml NGF (lane 2,+NGF); 100 μg/ml anti-LNGFR IgG (lane 3, REX IgG); 100 mg/ml RtrkA.EX IgG (lane 4, RTA IgG); 100 μg/ml nonimmune IgG (lane 5, Rabbit IgG); 67 μg/ml RtrkA.EX Fab (lane 6, RTA Fab). The arrows on the right indicate proteins which show increased tyrosine phosphoryation during the assay. Each of the PC12 cultures were treated for five minutes with NGF, or various antibody preparations, and changes in cellular tyrosine phosphorylation determined as described above.

Significant changes in phosphorylation were detected in response to NGF and the RtrkA.EX IgG preparation, and the RtrkA.EX IgG-induced pattern was indistinguishable from that found in response to NGF. In contrast, both control rabbit IgG and anti-LNGFR IgG were ineffective. Also, Fab fragments of the RtrkA.EX antibody had no effect.

To show that the RtrkA.EX IgG effects reflected activation of the trkA receptor, effects of NGF and various antibodies on trkA phosphotyrosine levels were examined. TrkA is a tyrosine kinase receptor which has been shown previously to be tyrosine phosphorylated and activated upon binding of NGF (Kaplan, et al., 1991b; Klein, et al., 1991). Therefore, PC12 cultures were treated as above with NGF, or antibody preparations, and then immunoprecipitated the trkA receptor from the corresponding lysates. The precipitates were analyzed by blotting with the anti-phosphotyrosine antibody.

RtrkA.EX IgG induces trXkA autophosphorylation. PC12 cells were treated as described above with: no addition (lane 1); 10 ng/ml NGF (lane 2); 200 mg/ml RtrkA.EX Fab (lane 3, RTA Fab); 200, 67, 22, and 7 $\mu$g/ml RtrkA.EX IgG (lanes 4–7, RTA IgG); and 200 $\mu$g/ml rabbit IgG (lane 8, Control IgG). TrkA receptor was immunoprecipitated from 250 $\mu$g of each lysate by the addition of rtrkA.cyt IgG and protein A-sepharose. The precipitations were separated on a 7.5% SDS gel and tyrosine phosphorylation detected as discussed in Example 3.

The RtrkA.EX IgG preparation induced a concentration-dependent increase in trkA tyrosine phosphorylation after five minutes, while the RtrkA.EX Fab preparation and control nonimmune IgG did not. A similar concentration of RtrkA.EX IgG was needed to promote maximal phosphorylation as is required to inhibit completely $^{125}$I-NGF binding (shown in FIG. 1A). In a related experiment, the effect of the RtrkA.EX IgG preparation was tested in parallel on the PC12 cell line and on the PC12nnr5 line, a derivative of PC12 cells which lacks detectable expression of trkA MRNA or protein (Loeb, et al., 1991). RtrkA.EX IgG was able to induce cellular phosphosphorylation in PC12 cells, but not in PC12nnr5. Transfection of trkA into PC12nnr5 restored its responsiveness to the RtrkA.EX IgG.

Example 5

RtrkA.EX Fab Inhibits and RtrkA.EX IgG Stimulates Survival of Neonatal Sympathetic Neurons To determine the effects of the trkA antibodies on long-term responses to NGF, a classic in vitro assay for NGF action was utilized: the NGF-dependent survival and process outgrowth of rat neonatal sympathetic neurons from the superior cervical ganglion. These cells are dependent on NGF during this period in vivo and in vitro. The withdrawal of NGF leads to a lack of process outgrowth and apoptotic cell death. Neonatal sympathetic neurons were isolated and then cultured in the presence of NGF, NGF plus control nonimmune Fab fragments, or NGF plus RtrkA.EX Fab fragments.

Neonatal rat sympathetic neurons were isolated from superior cervical ganglia of newborn rats as described (Hawrot, E. and Patterson, P. H., *Meth. Enzymol.,* 53, 574–584 (1979)). The ganglia were treated with 1 mg/ml collagenase/dispase in CMF-PBS (45 minutes at 37° C.; Boehringer Mannheim Biochemicals), and washed with the same buffer. The ganglia were triturated to remove the neurons, and the isolated cells washed several additional times in CMF-PBS. The cells were cultured on a collagen I substrate in a defined medium (Leibowitz L-15/$CO_2$ medium containing 1× nonessential amino acids, 1 mg/ml bovine serum albumin and 0.35% methocel, penicillin, streptomycin, glucose, and imidizole as described (Hawrot and Patterson, 1979).

In some of the RtrkA.EX IgG activation experiments, the medium contained in addition: stable vitamin mix, fresh vitamin mix (Hawrot and Patterson, 1979) and N1 supplement (Bottenstein, et al., *Exp. Cell Res.* 125:183–190 (1980)). Essentially identical results were obtained under either condition.

After 24 hours, the cultures were fixed with PBS containing 5% sucrose and 2.5% glutaraldehyde prior to photography and cell counts. Neurons were considered to have survived if they appeared phase-bright and had extended processes greater than two cell diameters in length.

As had been seen in the tyrosine phosphorylation assays, the RtrkA.EX Fab fragments were able to inhibit the NGF responses of these cells, as assayed by survival (FIG. 3) and neurite outgrowth.

FIG. 3 shows that RtrkA.EX Fab fragments inhibit NGF-dependent survival of sympathetic neurons. Isolated neurons from neonatal rat superior cervical ganglia were cultured in the presence or absence of 1 ng/ml NGF and 500 $\mu$g/ml nonimmune or RtrkA.EX Fab fragments as indicated. After 24 hours, the cultures were fixed and the number of process-bearing cells determined. The average and range from duplicate wells are shown.

Photomicrographs of sympathetic neurons cultured in the presence of (a) no addition; (b) NGF; (c) NGF+nonimmune Fab; (d) NGF+RtrkA.EX Fab were taken. NGF was added at 1 ng/ml, and the Fab fragments used at 500 $\mu$g/ml. After 24 hours, the cultures were fixed and photographed.

When the effect of the bivalent RtrkA.EX IgG preparation was tested quantitatively in the sympathetic neuronal survival assay, the RtrkA.EX antibody caused a small but reproducible decrease in NGF-dependent viability, while the anti-LNGFR and nonimmune IgG preparations had no obvious effects. However, when NGF was omitted from the culture medium, the RtrkA.EX antibody had a strong survival promoting activity, yielding a maximal survival of about 60% of that obtained with NGF and promoted extensive process outgrowth.

RtrkA.EX promotes survival of sympathetic neurons. Neonatal rat superior cervical ganglion neurons were cultured in combinations of NGF and IgG preparations as indicated. NGF was used at 50 ng/ml and the IgG preparations at 10 or 100 $\mu$g/ml. After 24 hours, the cultures were fixed and the number of process-bearing neurons counted.

Data was obtained from sympathetic neurons cultured in the presence of the following: (a) NGF; (b) NGF+normal rabbit IgG (Control IgG); (c) NGF+anti-LNGFR IgG (REX IgG); (d) NGF+RtrkA.EX IgG (RTA IgG); (e) no addition; (f) normal rabbit IgG; (g) anti-LNGFR IgG; and (h) RtrkA.EX IgG. The antibodies and NGF were added at 100 $\mu$g/ml and 50 ng/ml, respectively. Cultures were incubated 24 hours prior to fixation.

Neither the control IgG nor the anti-LNGFR antibody alone had any in vitro survival activity. In addition, RtrkA.EX Fab fragments were unable to support sympathetic neuron survival. The effects of RtrkA.EX IgG were also tested on cultures containing primed PC12 cells (PC12 cells which have been previously exposed to NGF for seven days, resulting in differentiation). The RtrkA.EX IgG showed a clear ability to promote neurite outgrowth of these cells in the absence of NGF; approximately 60% as many cells extended neurites as responded in the presence of NGF.

What is claimed is:

1. A method for activating a trk receptor comprising exposing cells having the trk receptor to a multivalent immunoglobulin which binds to the receptor and activates the receptor.

2. A method of claim 1 wherein the trk receptor is selected from the group consisting of trkA, trkB, and trkC.

3. A method of claim 1 wherein the immunoglobulin induces at least one member of the group consisting of an increase in phosphorylation of the receptor, an increase in phosphorylation of a protein substrate that is phosphorylated in response to activation of the receptor, and promotion of an effector function of receptor activation.

4. A method of claim 3 wherein the effector function is a member of the group consisting of promotion of neuronal survival, promotion of neuronal differentiation, and improved neuronal function.

5. A method of claim 1 wherein the immunoglobulin is bivalent.

6. A method of claim 1 wherein the immunoglobulin is a monoclonal antibody.

* * * * *